(12) United States Patent
Dietz et al.

(10) Patent No.: US 8,048,167 B2
(45) Date of Patent: Nov. 1, 2011

(54) ORTHOPAEDIC IMPLANT KIT, ORTHOPAEDIC SURGERY KIT AND ASSOCIATED METHOD

(75) Inventors: Terry L. Dietz, Columbia City, IN (US); John S. Wagley, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 514 days.

(21) Appl. No.: 11/215,929

(22) Filed: Aug. 30, 2005

(65) Prior Publication Data

US 2007/0050042 A1 Mar. 1, 2007

(51) Int. Cl.
*A61F 2/32* (2006.01)

(52) U.S. Cl. ................... 623/22.42; 623/22.11

(58) Field of Classification Search .......... 623/22.4, 623/22.41, 22.42, 22.45, 22.46, 23.46, 20.32, 623/23.15, 23.11, 22.21, 20.14, 20.15, 20.35, 623/20.34, 22.11–22.2, 19.11–19.14
See application file for complete search history.

(56) References Cited

U.S. PATENT DOCUMENTS

| | | | |
|---|---|---|---|
| 4,051,559 A | | 10/1977 | Pifferi |
| 4,608,055 A | * | 8/1986 | Morrey et al. ............ 623/22.46 |
| 4,619,659 A | * | 10/1986 | Witzel ...................... 623/23.36 |
| 4,624,673 A | | 11/1986 | Meyer |
| 4,728,335 A | * | 3/1988 | Jurgutis .................... 623/23.23 |
| 4,790,852 A | | 12/1988 | Noiles |
| 4,846,839 A | | 7/1989 | Noiles |
| 4,919,678 A | | 4/1990 | Kranz |
| 4,957,510 A | * | 9/1990 | Cremascoli .............. 623/22.46 |
| 4,963,155 A | | 10/1990 | Lazzeri et al. |
| 4,978,357 A | | 12/1990 | Goymann et al. |
| 5,002,578 A | * | 3/1991 | Luman ...................... 623/22.42 |
| 5,047,060 A | | 9/1991 | Henssge et al. |
| 5,080,685 A | | 1/1992 | Bolesky et al. |
| 5,181,928 A | | 1/1993 | Bolesky et al. |
| 5,286,260 A | | 2/1994 | Bolesky et al. |
| 5,370,706 A | | 12/1994 | Bolesky et al. |
| 5,580,352 A | | 12/1996 | Sekel |
| 5,645,607 A | | 7/1997 | Hickey |

(Continued)

FOREIGN PATENT DOCUMENTS

EP 0 201 407 A1 11/1986

(Continued)

OTHER PUBLICATIONS

Wright, Profemur Z Total Hip System, Wright Medical, Inc., Arlington, TN.

(Continued)

*Primary Examiner* — Alvin J Stewart

(57) ABSTRACT

A kit for use in performing revision surgery on a cavity in a canal of extending from a resected plane a long bone is provided. The kit includes a canal component fitted to the cavity. The canal component includes a canal portion having first and second ends. The canal component further includes a sleeve portion having an external periphery and an internal periphery defining an internal cavity. The kit also includes a first joint component having a body portion and a connection portion. The connection portion is fitted into the sleeve portion. A connection portion of a second joint component also may be fitted into the sleeve portion so that the external periphery of the connection portion of the first joint component is spaced inwardly from the external periphery of the sleeve portion of the canal component when the first joint component is fixedly connected to the canal.

15 Claims, 26 Drawing Sheets

U.S. PATENT DOCUMENTS

| | | | | |
|---|---|---|---|---|
| 5,653,764 | A * | 8/1997 | Murphy | 623/23.15 |
| 5,653,765 | A * | 8/1997 | McTighe et al. | 623/22.42 |
| 5,725,592 | A * | 3/1998 | White et al. | 623/23.35 |
| 5,858,020 | A * | 1/1999 | Johnson et al. | 623/23.15 |
| 5,871,549 | A * | 2/1999 | Jayashankar et al. | 623/22.4 |
| 5,876,459 | A * | 3/1999 | Powell | 623/23.15 |
| 5,902,340 | A * | 5/1999 | White et al. | 128/898 |
| 5,906,644 | A * | 5/1999 | Powell | 623/20.15 |
| 5,910,171 | A * | 6/1999 | Kummer et al. | 623/18.11 |
| 5,935,172 | A * | 8/1999 | Ochoa et al. | 623/23.36 |
| 6,126,691 | A | 10/2000 | Kasra et al. | |
| 6,214,053 | B1 * | 4/2001 | Ling et al. | 623/23.11 |
| 6,217,620 | B1 * | 4/2001 | Park | 623/23.26 |
| 6,264,699 | B1 * | 7/2001 | Noiles et al. | 623/23.23 |
| 6,319,286 | B1 * | 11/2001 | Fernandez et al. | 623/23.18 |
| 6,361,566 | B1 * | 3/2002 | Al-Hafez | 623/22.15 |
| 6,428,578 | B2 * | 8/2002 | White | 623/23.22 |
| 6,432,110 | B1 | 8/2002 | Richelsoph | |
| 6,440,171 | B1 * | 8/2002 | Doubler et al. | 623/22.42 |
| 6,464,728 | B1 | 10/2002 | Murray | |
| 6,497,728 | B2 * | 12/2002 | Yong | 623/23.46 |
| 6,524,344 | B2 * | 2/2003 | Yoon | 623/23.46 |
| 6,669,728 | B2 | 12/2003 | Despres, III et al. | |
| 6,682,568 | B2 * | 1/2004 | Despres et al. | 623/22.42 |
| 6,692,530 | B2 * | 2/2004 | Doubler et al. | 623/22.42 |
| 6,699,293 | B2 | 3/2004 | White | |
| 6,702,854 | B1 * | 3/2004 | Cheal et al. | 623/22.42 |
| 6,706,072 | B2 * | 3/2004 | Dwyer et al. | 623/22.42 |
| 6,716,250 | B2 * | 4/2004 | Ganjianpour | 623/22.42 |
| 6,723,129 | B2 * | 4/2004 | Dwyer et al. | 623/22.42 |
| 6,783,548 | B2 | 8/2004 | Hyde, Jr. | |
| 7,033,399 | B2 * | 4/2006 | Doubler et al. | 623/22.42 |
| 7,044,975 | B2 * | 5/2006 | Cheal et al. | 623/22.42 |
| 7,122,056 | B2 * | 10/2006 | Dwyer et al. | 623/22.43 |
| 7,135,044 | B2 * | 11/2006 | Bassik et al. | 623/22.42 |
| 2002/0004685 | A1 | 1/2002 | White | |
| 2002/0040244 | A1 * | 4/2002 | Despres et al. | 623/22.15 |
| 2002/0042655 | A1 | 4/2002 | Hayes, Jr. et al. | |
| 2002/0058999 | A1 | 5/2002 | Dwyer et al. | |
| 2002/0059000 | A1 | 5/2002 | Dwyer et al. | |
| 2002/0111689 | A1 | 8/2002 | Hyde, Jr. | |
| 2002/0120343 | A1 * | 8/2002 | Doubler et al. | 623/22.42 |
| 2002/0151984 | A1 | 10/2002 | White | |
| 2003/0074079 | A1 * | 4/2003 | McTighe et al. | 623/22.42 |
| 2003/0074080 | A1 | 4/2003 | Murray | |
| 2003/0088316 | A1 | 5/2003 | Ganjianpour | |
| 2003/0195635 | A1 | 10/2003 | Crofford | |
| 2003/0204266 | A1 | 10/2003 | Gerbec et al. | |
| 2003/0204268 | A1 | 10/2003 | Gerbec et al. | |
| 2003/0204269 | A1 | 10/2003 | Gerbec et al. | |
| 2004/0010319 | A1 | 1/2004 | McTighe et al. | |
| 2004/0054419 | A1 * | 3/2004 | Serra et al. | 623/22.42 |
| 2004/0098134 | A1 | 5/2004 | Meulink | |
| 2004/0107001 | A1 * | 6/2004 | Cheal et al. | 623/22.42 |
| 2004/0117023 | A1 | 6/2004 | Gerbec et al. | |
| 2004/0117024 | A1 | 6/2004 | Gerbec et al. | |
| 2004/0122440 | A1 | 6/2004 | Daniels et al. | |
| 2004/0122525 | A1 | 6/2004 | Daniels et al. | |
| 2004/0127910 | A1 * | 7/2004 | Pubols et al. | 606/99 |
| 2004/0172139 | A1 * | 9/2004 | Dwyer et al. | 623/22.43 |
| 2005/0288791 | A1 | 12/2005 | Tornier et al. | |
| 2006/0142872 | A1 | 6/2006 | Klotz et al. | |
| 2007/0043447 | A1 | 2/2007 | Cheal et al. | |
| 2007/0050040 | A1 | 3/2007 | Guederian et al. | |

FOREIGN PATENT DOCUMENTS

| | | |
|---|---|---|
| EP | 0257359 A1 | 2/1988 |
| EP | 0 421 008 A1 | 4/1991 |
| EP | 0257359 B1 | 11/1991 |
| EP | 0679375 B1 | 11/1995 |
| EP | 0 695 540 A1 | 2/1996 |
| EP | 0 788 773 A1 | 8/1997 |
| EP | 1004283 A2 | 5/2000 |
| EP | 1437103 A2 | 7/2004 |
| EP | 1437106 A2 | 7/2004 |
| EP | 1 566 155 A1 | 8/2005 |
| FR | 2 647 669 A | 12/1990 |
| FR | 2 697 996 A | 5/1994 |
| WO | WO 95/13757 A1 | 5/1995 |
| WO | WO 98/08467 A1 | 3/1998 |
| WO | WO 98/08468 A1 | 3/1998 |
| WO | WO 02/07653 A1 | 1/2002 |
| WO | WO 02/067811 A2 | 9/2002 |

OTHER PUBLICATIONS

Joint Medical Products Corp (Now Known as De Puy Orthopaedics), S-ROM Total Hip System, 1993, 15, Joint Medical Products Corporation, Stamford, CT (Now DePuy Orthopaedics, 700 Orthopaedic Drive, Warsaw, IN).

European Search Report for European Patent Application No. 06254386.3-1269, Dated Oct. 28, 2010, 7 Pages.

Japanese Search Report for Corresponding Application No. 2006-231972, Dated Mar. 29, 2011, 4 Pages.

Japanese Search Report for Corresponding Application No. 2006-231984, Dated Mar. 29, 2011, 3 Pages.

* cited by examiner

ORTHOPAEDIC IMPLANT KIT, ORTHOPAEDIC SURGERY KIT AND ASSOCIATED METHOD

CROSS-REFERENCE TO RELATED APPLICATIONS

Cross reference is made to the following applications: DEP 5419USNP titled "ORTHOPAEDIC IMPLANT, STEM AND ASSOCIATED METHOD", U.S. patent application Ser. No. 11/216,588 filed on Aug. 30, 2005 and DEP5557USNP titled "ORTHOPAEDIC IMPLANT STEM COMPONENT, JOINT COMPONENT, AND ASSOCIATED KIT", U.S. patent application Ser. No. 11/216,396 filed on Aug. 30, 2005 filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

Currently in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck offsets, head offsets and leg lengths. The combination of these four factors affects the laxity of the soft tissue. By optimizing the biomechanics, the surgeon can provide a patient a stable hip much more resistant to dislocation. In order to accommodate the range of patient arthropometrics, a wide range of hip implant geometries are currently manufactured by DePuy Orthopaedics, Inc., the assignee of the current application, and by other companies. In particular, the S-ROM® total hip systems offered by DePuy Orthopaedics, Inc. include three offsets, three neck lengths, four head lengths and one leg length adjustment. The combination of all these biomechanic options is rather complex.

Anteversion of a total hip system is closely linked to the stability of the joint. Improper version can lead to dislocation and patient dissatisfaction. Version control is important in all hip stems. However, it is a more challenging issue with the advent of stems with additional modularity.

The prior art has provided for some addressing of the anteversion problem. For example, the current S-ROM® stems have laser markings on the medial stem and the proximal sleeve. This marking enables the surgeon to measure relative alignment between these components. Since the sleeve has infinite anteversion, it is not necessarily oriented relative to a bony landmark that can be used to define anteversion. In fact, the current sleeves are sometimes oriented with the spout pointing directly laterally into the remaining available bone.

Prior art stems may be aligned relative to a patient's bony landmarks. These stems are monolithic. They cannot locate the neck independently of the distal stem. Therefore, anteversion is limited. Most bowed, monolithic stems are sold in fixed anteversion; for example, at an anteversion of 15 degrees. These monolithic stems have limited flexibility for rotational alignment since the distal stem must follow the bow of the patient's femur and this may not provide an operable biomechanical result.

In a common step in the surgical procedure known as total hip arthroplasty, a trial or substitute stem is first implanted into the patient. The trial is utilized to verify the selected size and shape of the implant in situ on the patient and the patient is subjected to what is known as a trial reduction. This trial reduction represents moving the joint, including the trial implant through selected typical motions for that joint. Current hip instruments provide a series of trials of different sizes to help the surgeon assess the fit and position of the implant. Trials, which are also known as provisionals, allow the surgeon to perform a trial reduction to assess the suitability of the implant and implant's stability prior to final implant selection.

Most hip stems implanted currently are of a one-piece or mono-block design. Mono-block hip stem designs allow for no adjustments. Thus, they require that the hip stem be removed and replaced to adjust head height or offset. Also, mono-block stems are not designed to be used in minimally invasive surgery and are not optimal for use with minimally invasive surgery procedures.

Surgical variables such as leg length discrepancy may result in surgical error that may need to be corrected or optimized. Further, due to implant subsidence during the use of an implant, the head-height at a revision surgery may need to be corrected. Further, revision surgery may be required to correct the instability of the hip joint. Stability may be restored by moving the head proximally and or increasing the offset of the implant to tighten the soft tissues. These corrections may be made at revision surgery to address these dislocations, however with current mono-block stems the stem must be removed from the femur to accomplish these changes in the implant configuration. Such removal of the stem from the femur may make the revision surgery quite difficult in that the stem tends to engrow with the tissues of the bone. Also, removal of the stem may lead to significant loss of bone, which can compromise the fixation of the stem upon re-implantation.

Further revision surgery may be required to correct weak abductor function by increasing the offset of the stem. The changing in a revision surgery to an increased offset stem may require that the stem be removed from the medullary canal of the femur and replaced with a stem with a different offset.

Further mono-block stems are not easily used in minimally invasive hip procedures where the incision through the skin and soft tissue is minimized. The surgeon may have difficulty to work in the joint space after the stem is in place. The neck of the mono-block stem may be in the way during the performance of the surgery.

In order to reduce inventory costs and complexity, many trialing systems are modular. For example, in the Excel Instrument System, a product of DePuy Orthopaedics, Inc., there is a series of broaches and neck trials that can be mixed and matched to represent the full range of implants. There is a single fixed relationship between a broach and a neck trial, because these trials represent a system of monolithic stem implants.

Likewise, in the current S-ROM® instrument systems provided by DePuy Orthopaedics, Inc., there are neck, proximal body, distal stem, head and sleeve trials. By combining all these components, the implant is represented. Since the S-ROM® stem is modular and includes a stem and a sleeve, the angular relationship or relative anteversion between the neck and the sleeve is independent and represented by teeth mating between the neck and the proximal body trial. The proximal body trial has fixed transverse bolts that are keyed to the sleeve in the trialing for straight, primary stems. The long stem trials do not have the transverse bolts and are thus not rotationally stable during trial reduction and therefore are not always used by the surgeon.

Prosthetic joint implants are currently surging in use and technology. In performing most prosthetic joint implants, what is known as a 'trial' or 'provisional' is used before a final prosthesis is used. The trial or provisional is used to select the proper joint prosthesis and/or to orient or align one or more of the components of the final joint prosthesis. The trial or trial components are temporarily implanted to achieve proper sizing, placement and/or orientation of the final joint prosthesis, as well as achieve anatomical orientation of the prosthesis and/or components of the joint prosthesis.

Hip arthroplasty provisionals or trials have a neck that is used to attach a femoral head provisional or trial thereto. The orientation of the neck relative to the shaft of the broach or trial is described in terms of anteversion, neck length, neck angle, and/or neck offset. Because each patient's original femoral neck anatomy is different, the ability to replicate the original femoral neck anatomy of each patient during hip arthroplasty requires multiple neck trials having various orientations. The use of multiple neck segments is not advantageous since it requires more time, increased instrument cost and increased space in the instrument sterilization case.

Thus, trialing systems utilized by many hip implants or prostheses generally consist of a broach and a neck segment. In order to intraoperatively change the offset of the trial (i.e. neck segment and broach), the neck trial must be removed and another neck trial must be put in its place. Thus, multiple neck trials that are exchangeable with one another relative to the broach are necessary in order to replicate the original hip anatomy.

Other hip systems utilize only one neck segment with the offset incorporated into the location of the trunnion of the broach. This design, however, does not mimic the exact geometry of the actual implant. While it is desired to be able to try several neck offsets relative to the broach in order to achieve a proper head positioning for the final implant, the prior art is deficient.

In U.S. Pat. No. 5,645,607 issued to Hickey, a hip trial or prosthesis having an adjustable neck portion is disclosed in which the problem of multiple neck trials is addressed. The adjustable neck of Hickey allows the trialing of various neck offsets in order to achieve a correspondence between the spatial orientation of a patient's original anatomy and a final implanted hip ball prosthesis.

However, Hickey requires a vertical height change of the neck segment in order to move between the various offsets. Where vertical height is restricted during surgery, especially in current, less invasive arthroplasty procedures, vertical height adjustment is undesirable.

There are a variety of modular stem designs in the prior art. Most of these designs focus on the ability to use varying stem diameters and length with various size proximal bodies to provide optimal fill on both the diaphysis and the metaphysis simultaneously (to optimize fixation of the device). In many of these designs the neck cannot be removed or replaced to adjust head-height or offset without disturbing the fixation of at least the modular proximal body portion of the stem. Prior art modular stems include the modular stem as disclosed in U.S. Pat. No. 5,370,706 to Bolesky, et al. and assigned to the applicant of the instant application. The Bolesky patent, U.S. Pat. No. 5,370,706 is hereby incorporated in its entirety by reference.

Another modular stem available in the prior art is the S-ROM® stem sold by DePuy Orthopaedics, Inc., Warsaw, Ind. and described in U.S. Pat. Nos. 4,624,673, 4,790,852, and 4,846,839. The U.S. Pat. Nos. 4,624,673, 4,790,852, and 4,846,839 are incorporated herein by reference in their entireties.

The prior art further includes a modular stem marketed by Wright Medical, Inc. of Arlington, Tenn. The Pro-Femur Stem provides a modular neck with a taper on both ends, one to engage the stem proximal body and one to engage the head. The present invention is adapted to solve at least some of the aforementioned problems with the prior art.

SUMMARY OF THE INVENTION

An aspect of the present invention is in the form of a hip stem that utilizes a modular neck portion. The hip stem includes two main parts. These parts are a hip stem body and a modular neck portion. The modular neck provides the surgeon the ability to adjust the proximal-distal head height and the head offset. These adjustments may be either independent or in combination with each other. The adjustment can be made after the stem is seated and fixed into place, eliminating the need to disturb the fixation of the stem. The adjustment can take place as fine tuning at the end of the initial orthopaedic surgery or upon a revision surgery when it is determined that the cause for the revision (such as instability or leg length discrepancy) may be addressed by adjustment.

The design of an aspect of the present invention allows the stem body to be implanted separately from the modular neck portion. This feature may be advantageous in minimally invasive surgery where smaller components may be easier to place through smaller incisions and where waiting until near the end of the operation to implant the neck portion provides more room for the surgeon to work and better access to the joint space.

According to yet another aspect of the present invention, the hip stem design includes two main parts, a hip stem body and a modular neck portion. The modular neck portion fits within a recess in the top of the stem body. This modular design allows the modular neck portion to be placed or removed without disturbing the fixation of the stem body in the bone. A variety of methods can be used to obtain mechanical attachment of the modular stem portion to the body.

For example, in one embodiment of the present invention, dowel pins are pressed into one side of the interface with a tight slip fit on the other side to align and aid in carrying bending moments across the interface. This design ensures that the screw (which is used to apply the compressive locking forces across the interface) is subjected only to axial tension loads. By eliminating bending moments in the screw, fatigue failure of the thread fastener can be better avoided.

According to another aspect of the present invention, a means for holding the screw captive in the modular stem portion may be desirable to aid in assembling the modular stem portion to the stem body. Such capture of the screw would minimize the number of parts to be handled and eliminate the need to handle or assemble many small pieces.

In yet another embodiment of the present invention, the dowel pins are replaced with tapers, which may be either rectangular or cylindrical. The tapers serve to align the parts and carry any bending moments so that the screw is subjected to only axial tension loads.

In yet another aspect, the present invention provides a hip stem for use in performing hip arthroplasty. The hip stem is to be fitted to a cavity in the canal of a femur. The hip stem includes a stem component including a distal stem portion and a proximal body portion. The hip stem also includes a neck component fixedly connectable to the stem component. The neck component includes a proximal neck portion and a distal body portion. The neck component is adapted for removal from the femur without disturbing the fixation of the stem component to the bone.

In another aspect, the present invention provides a hip prosthesis for use in performing hip arthroplasty. The hip stem is fitted to a cavity in the canal of a femur. The hip prosthesis includes an acetabular cup, a head, a neck component and a stem component. The stem component includes a distal stem portion and a proximal body portion. The neck component is fixedly connectable to the stem component. The neck component includes a proximal neck portion and a distal body portion. The neck component is adapted for removal from the femur without disturbing the fixation of the stem component to the bone.

In another aspect, the present invention provides a kit for performing revision surgery. The kit includes a stem component having a distal stem portion and a proximal body portion. The kit also includes a first neck component fixedly connectable to the stem component. The first neck component includes a proximal neck portion and a distal body portion. The first neck component is adapted for removal from the femur without disturbing the fixation of the stem component to the bone. The kit also includes a second neck component fixedly connectable to the stem component. The second neck component includes a proximal neck portion and a distal body portion. The second neck component is adapted for removal from the femur without disturbing the fixation of bone surrounding the stem component.

In another aspect, the present invention provides an orthopaedic implant for use in performing joint arthroplasty. A portion of the orthopaedic implant is to be fitted to a cavity in the canal of a long bone. The orthopaedic implant includes a stem component having a stem portion and a body portion. The orthopaedic implant also includes a joint component fixedly connectable to the stem component. The joint component has an articulation portion and a connection portion. The joint component is adapted for removal from the long bone without disturbing the fixation of bone surrounding the stem.

In another aspect, the present invention provides a stem component for use with a joint component having an articulation portion and a connection portion in performing joint arthroplasty. At least a portion of the stem component is to be fitted to a cavity in the canal of a long bone. The stem component includes a stem portion and a body portion. The body portion is adapted to permit removal of the connection portion of the joint component from the long bone without disturbing the fixation of bone surrounding the joint component.

In another aspect, the present invention provides a joint component for use with a stem component having a body portion and a stem portion in performing joint arthroplasty. At least a portion of the stem component is to be fitted to a cavity in the canal of a long bone. The joint component includes a connection portion and an articulation portion. The connection portion is adapted to permit the removal of the joint component from the long bone without disturbing the fixation of bone surrounding the joint component.

In another aspect, the present invention provides an orthopaedic implant trial for use in performing joint arthroplasty and to assist in performing a trial reduction in performing joint arthroplasty. A portion of the orthopaedic implant trial is fitted to a cavity in the canal of a long bone. The orthopaedic implant trial includes a stem component having a stem portion and a body portion. The orthopaedic implant trial also includes a joint component fixedly connectable to the stem component. The joint component has an articulation portion and a connection portion. A portion of the body portion of the stem component extends over a portion of the connection portion of the joint component.

In another aspect, the present invention provides a kit for use in performing joint arthroplasty. The kit includes an orthopaedic implant trial for use in performing joint arthroplasty. The trial is to be fitted to a cavity in the canal of a long bone and to assist in performing a trial reduction in performing joint arthroplasty. The orthopaedic implant trial includes a stem component having a stem portion and a body portion. The orthopaedic implant trial also includes a joint component fixedly connectable to the stem component. The joint component has an articulation portion and a connection portion. The joint component is adapted for removal from the long bone without disturbing the fixation of the stem component to the bone. The kit includes an orthopaedic implant for use in performing joint arthroplasty. A portion of the orthopaedic implant is fitted to a cavity in the canal of a long bone. The orthopaedic implant includes a stem component having a stem portion and a body portion. The orthopaedic implant also includes a joint component fixedly connectable to the stem component. The joint component includes an articulation portion and a connection portion. The joint component is adapted for removal from the long bone without disturbing the fixation of bone surrounding the joint component.

In another aspect, the present invention provides a method for treating orthopaedic joint disease of a patient. The method includes the step of implanting an orthopaedic implant into a cavity in the canal of a long bone. The orthopaedic implant includes a stem component and a first joint component fixedly connectable to the stem component. The joint component is adapted for removal from the long bone without disturbing the fixation of the stem component to the bone. The method also includes the steps of monitoring the condition of the patient and determining that the patient needs a revision prosthesis. The method also includes the steps of providing a second joint component compatible with the stem component and removing the first joint component from the stem component of the orthopaedic implant in vivo in the patient without disturbing the fixation of bone surrounding the orthopaedic implant. The method also includes the step of implanting the second joint component into the stem component in vivo in the patient.

In another aspect, the present invention provides a method for providing revision joint arthroplasty on a patient having an orthopaedic implant. The orthopaedic implant includes a stem component and a first joint component fixedly connectable to the stem component. The joint component is adapted for removal from the long bone without disturbing the fixation of the stem component to the bone. The method includes the steps of monitoring the condition of the patient and determining that the patient needs a revision prosthesis. The method also includes the steps of providing a second joint component compatible with the stem component and removing the first joint component from the stem component of the orthopaedic implant in vivo in the patient without disturbing the fixation of bone surrounding the orthopaedic implant. The method also includes the step of implanting the second joint component into the stem component in vivo in the patient.

In another aspect of the present invention an orthopaedic implant for use in performing joint arthroplasty is provided. A portion of the implant is fitted to a cavity in the canal of a long bone. The cavity extends from a resected plane of the long bone. The implant includes a joint component having a stem element with an external periphery. The stem element defines a distal end for insertion into the cavity. The external periphery of the stem element has a resection ring that aligns with the resected plane of the long bone and a body element fixedly connectable to the stem element. The body element has a external periphery. A distal portion of the body element extends from the resection ring toward the distal end of the stem element. The periphery of the body element is spaced from the external periphery of the stem element so that the body element may be removed without disturbing the fixation.

According to yet another aspect of the present invention an orthopaedic implant stem for use in performing joint arthroplasty is provided. A portion of the orthopaedic implant stem is to be fitted to a cavity in the canal of a long bone. The orthopaedic implant stem includes a distal element defining an external periphery of the distal element. The distal element defines a distal end of the element for insertion into the cavity and an opposed connection end. The distal element defines a recess therein extending from the opposed connection end of the distal element. The orthopaedic implant stem component also includes a proximal element fixedly connectable to the distal element. A distal portion of the proximal element extends generally from the connection end of the distal element toward the distal end of the distal element when the proximal element is fixedly connected to the stem. The distal portion of the proximal element is spaced inwardly from the external periphery of the distal element when the proximal element is fixedly connected to the stem component so that the proximal element may be removed from the long bone without disturbing the fixation of the distal element to the long bone.

According to another aspect of the present invention a method for treating orthopaedic joint disease of a patient is provided. The method includes the steps of resecting a long bone along a resection plane and preparing a cavity in the canal of the long bone. The method includes the step of implanting an orthopaedic implant into a cavity in the canal of a long bone. The orthopaedic implant includes a joint component having a stem element and a first body element fixedly connectable to the stem element. The orthopaedic implant is secured in the canal of the long bone with the body element being spaced from the long bone. The method further includes the steps of monitoring the condition of the patient, determining that the patient needs a revision prosthesis, providing a second body element compatible with the stem element, and removing the first body element from the stem element of the orthopaedic implant in vivo in the patient without disturbing the fixation of bone surrounding the stem element of the orthopaedic implant and without damaging bone surrounding the first body element. The method also includes the step of implanting the second body element into the stem element in vivo in the patient.

According to yet another aspect of the present invention an orthopaedic implant for use in performing joint arthroplasty is provided. A portion of the orthopaedic implant is capable of being fitted to a cavity in the canal of a long bone. The cavity extends from a resected plane of the long bone. The orthopaedic implant includes a joint component. The joint component includes a stem element defining an external periphery of the stem element. The stem element has a first end for insertion into the cavity. The external periphery of the stem element has a stem resection ring. The stem resection ring may be aligned with the resected plane of the long bone. The joint component also includes a body element, which is capable of being fixedly fitted to the stem element. The body element includes an external periphery. The external periphery of the body element has a body resection ring. The body resection ring may be aligned with the resected plane of the long bone. A canal portion of the body element extends generally from the resection ring of the external periphery of the body element toward the first end of the stem element when the body element is fixedly connected to the stem element. The external periphery of the canal portion of the body element is spaced inwardly from the external periphery of the stem element when the body element is fixedly connected to the stem so that the body element may be removed from the long bone without disturbing the fixation of the stem element to the long bone.

According to a further aspect of the present invention an orthopaedic implant stem for use in performing joint arthroplasty is provided. A portion of the orthopaedic implant stem may be fitted to a cavity in the canal of a long bone. The orthopaedic implant stem includes a canal element having an external periphery. The canal element has a first end for insertion into the cavity and an opposed connection end. The canal element has a recess extending from the opposed connection end of the canal element. The recess has a internal periphery. The canal element also has an external periphery spaced outwardly from the internal periphery of the recess. The orthopaedic implant stem further includes a body element that may be fixedly connected to the canal element. A first portion of the body element may be inserted into the recess of the canal element when the first element is fixedly connected to the canal element. The first portion of the body element is spaced inwardly from the external periphery of the canal element when the body element is fixedly connected to the canal element so that the body element may be removed from the long bone without disturbing the fixation of the canal element to the long bone.

According to a another aspect of the present invention a method for treating orthopaedic joint disease of a patient is provided. The method includes the steps of resecting a long bone along a resection plane and preparing a cavity in the canal of the long bone. The method also includes the step of implanting an orthopaedic implant into a cavity in the canal of the long bone. The orthopaedic implant includes a joint component having a canal element and a first body element. The first body element may be fixedly connected to the canal element. The orthopaedic implant is secured in the canal of the long bone with the first body element being spaced from the long bone. The method further includes the steps of monitoring the condition of the patient and determining that the patient needs a revision prosthesis. The method also includes the steps of providing a second body element connectable to the canal element and removing the first body element from the canal element of the orthopaedic implant in vivo without disturbing the fixation of bone surrounding the canal element of the orthopaedic implant and without damaging bone surrounding the first body element. The method further includes the step of implanting the second body element into the canal element in vivo.

The technical advantages of the present invention include the ability to independently adjust the head-height and the head offset without disturbing the fixation of the stem in the bone. For example, according to one aspect of the present invention a hip stem is provided including a stem component including a distal stem portion and a proximal body portion and a neck component. The neck component is fixably connected to the stem component. The neck component includes a proximal neck portion and a distal body portion. The neck component is adapted for removal from the femur without disturbing the fixation of the stem component to the bone. Thus, the present invention provides for the ability to independently adjust the head-height and the head offset without disturbing the fixation in the stem of the stem in the bone by merely changing the neck component by removing the neck component from the stem component while the stem component is in position in the bone.

The technical advantages of the present invention further include the ability to enhance minimally invasive hip procedures by having smaller incisions for the stem and neck. For example, according to another aspect of the present invention, a hip stem is provided including a stem component having a distal stem component and a proximal body portion and a neck component. The neck component is fixably connectable to the stem component. The neck component includes a proximal neck portion and a distal body portion. The neck component is adapted for removal from the femur without disturbing the fixation of the stem component to the bone. The stem component may thus be first inserted into the incision, put in position and then the neck component may be secured to the stem component. Thus the present invention provides for the enhancing of minimally invasive hip procedures by having smaller incisions for the stem and body. By allowing the neck portion to be inserted separately from the stem body, the implants may be inserted through a smaller incision with reduced soft tissue stretching and allowing the surgeon more space to work within the joint space until later in the procedure when the neck portion is inserted. In other words, the stem may be positioned in the incision and through the soft tissue put in place in the canal of the long bone and, in fact, cemented into position and permitted to be fixably secured into the proper position. At that time, the neck portion may then be inserted through the incision and the procedure continued.

The technical advantages of the present invention include the ability to permit common hip prostheses to be used for right and left hand versions of the hip prosthesis. For example, according to yet another aspect of the invention, a hip stem is provided with a stem component and a neck component. At least one of the stem component and the neck component are adapted to permit the stem component and neck component to have a first assembly relationship as well as a second assembly relationship which is different than the first assembly relationship. Thus the present invention provides for a hip stem assembly that permits both right and left hand versions with a common set of hip stem components.

The technical advantages of the present invention further include the ability to correct surgical error or optimize the surgical variables such as leg length discrepancy. For example, according to yet another aspect of the present invention, a hip stem is provided including a hip stem component and a neck component. The neck component is adapted for removal from the femur without disturbing the fixation of the stem component to the bone. Thus, the present invention provides for the replacement of the neck from the stem with the replacement neck having a different neck length than the replaced neck while replacing the neck with the stem in place. Thus the present invention provides for the correction of surgical error or optimization of a surgical variable such as leg length discrepancy.

The technical advantages of the present invention also include the ability to correct head height at revision surgery due to implant subsidence. For example, according to yet another aspect of the present invention, a hip stem is provided including a stem component and a neck component. The neck component is adapted for removal from the femur without disturbing the fixation of the stem component to the bone. Thus, the present invention provides for a replacement of the neck component with a replacement neck component with a different head-height than the initial neck component while having the stem component remain in place on the bone. Thus, the present invention provides for a correction of head height at revision surgery to adjust for implant subsidence.

The technical advantages of the present invention include the ability to correct instability of the hip joint. Stability may be restored by moving the head proximally and/or increasing the offset to tighten the soft tissue. The corrections can also be made at revision surgery to address dislocations. For example, according to yet another aspect of the present invention, a hip stem is provided including a stem component as well as a plurality of neck components. One of the pluralities of neck components may have a first offset dimension and the second component have a greater offset dimension. Thus, the present invention provides for replacing the first neck component with a second neck component with greater offset while having the stem remain in place on the bone. Thus, the present invention provides for the correction of instability by moving the head proximally or increasing the offset to tighten the soft tissues.

The technical advantages also include the ability to correct weak abductor function by increasing the offset of the hip stem, which increases the efficiency of the abductor muscles by increasing the moment arm of the abductor muscle action For example, according to yet another aspect of the present invention, a hip stem is provided including a stem component and a first neck component having a first offset and a second neck component having a greater offset than the first neck component. The neck component is adapted for removal from the femur without disturbing the fixation of the stem component to the bone. Thus, the present invention provides for replacing a first neck component with a second neck component of greater offset while the stem is in place in the bone. Thus, the present invention provides for correction of weak abductor function by increasing the offset of the hip stem.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
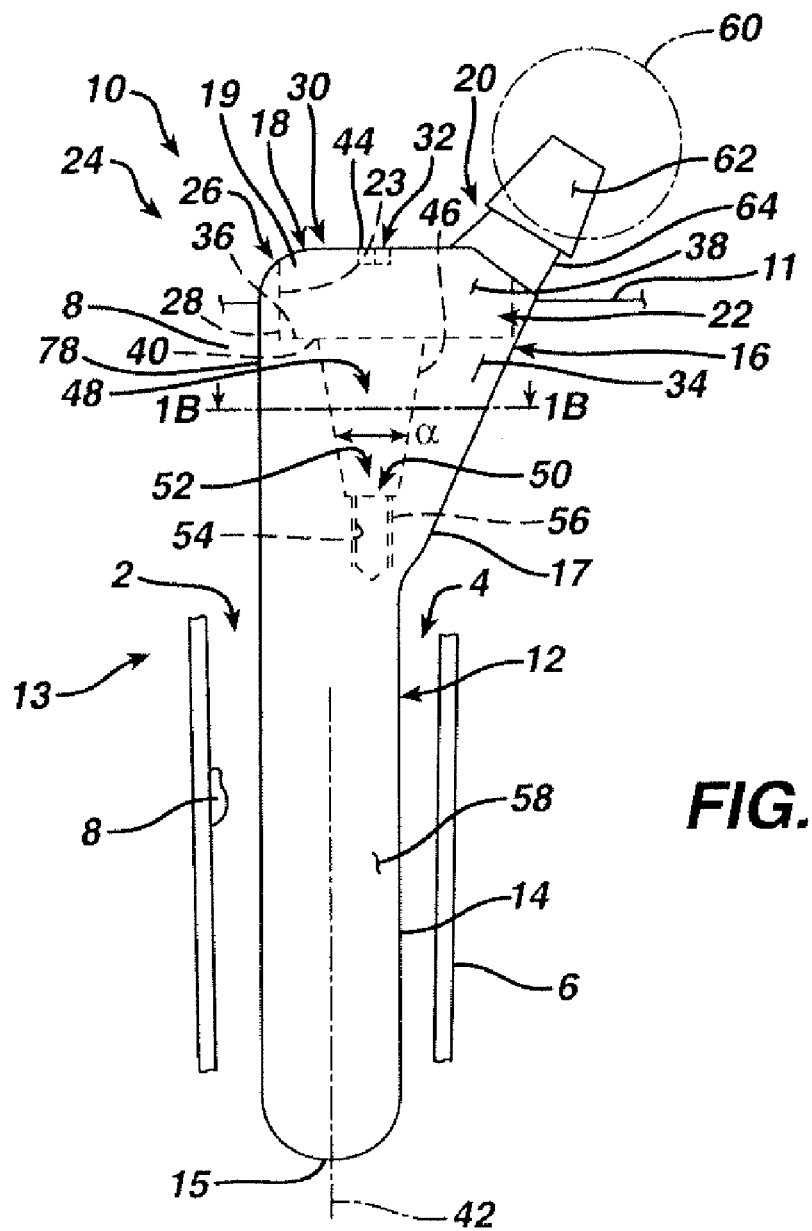
FIG. 1 is a plan view of a modular hip stem in accordance with an embodiment of the present invention utilizing a tapered lock and screw.

According to the present invention and referring now to FIG. 1, an embodiment of the present invention is shown as hip stem 10. Hip stem 10 is utilized for performing hip arthroplasty. The hip stem 10 is designed to be fitted into a cavity 2 in the canal 4 of a long bone 6, for example, the femur. The hip stem 10 includes a stem component 12 including a distal stem portion 14 and a proximal body portion 16. The hip stem 10 further includes a neck component 18 which, is as shown in FIG. 1, is fixedly connectable to the stem component 12. The neck component 18 includes a proximal neck portion 20 and a distal body portion 22. The neck component 18 is adapted for removal from the femur 6 without disruption of bone 8 around the stem component 12.

To provide for the removal of the neck component without disturbing the fixation of the stem component 12 to the bone 8, the hip stem 10 of the present invention may be adapted to provide all the support for the hip stem and fixation of the hip stem 10 to the femur 6 with the stem component 12. Thus, as shown in FIG. 1, the stem component 12 is configured, preferably, to provide as much support as possible for the hip stem 10 to the femur 6. For example, and as shown in FIG. 1, a portion 24 of the proximal body portion 16 of the stem component 12 extends over a portion of the distal body portion 22 of the neck component 18.

While the portion 24 of the proximal body portion of the stem component 12 may be positioned anywhere around the femur 6 to provide additional support for the stem component 12, it should be appreciated, and referring to FIG. 1, the portion 24 may extend substantially around the periphery of the femur 6.

For example, and as shown in FIG. 1, the stem component 12 may include a sleeve portion 26 extending proximally from the proximal body portion 16 of the stem component 12. The sleeve portion 26 may extend laterally, medially, anteriorly, or posteriorly or a combination thereof. For example, and as shown in FIG. 1, the sleeve portion 26 extends substantially around periphery 28 of the distal body portion 22 of the neck component 18.

As shown in FIG. 1, the distal body portion 22 of the neck component 18 may receive the stem component 12. To accommodate the neck component 18, the proximal body portion 16 of the stem component 12 may define a pocket 32 in the proximal body portion 16 for receiving the neck component 18.

As shown in FIG. 1, the hip stem 10 may be configured to assist in the removal of the neck component 18 from the femur 6 without disturbing the fixation of the stem component to the bone 8, the neck component 18 may be spaced from the femur. By spacing the neck component 18 from the femur, the neck component 18 may be removed without disturbing the fixation of the stem component 12 to the bone.

As shown in FIG. 1, the distal body portion 22 of the neck component 18 is removably secured to the proximal body portion 16 of the stem component 12. The distal body portion 22 and the proximal body portion 16 may be removably secured to each other in any reasonable manner.

For example, and as shown in FIG. 1, the proximal body portion 16 of the stem component 12 includes a periphery 34 of the proximal body portion 16. A portion 36 of the periphery 34 is generally planer. Similarly, the distal body portion 22 of the neck component 18 defines a periphery 38 of the distal body portion. A portion 40 of the periphery 38 is generally planer. The neck planer portion 40 and the body planer portion 36 are in contact with each other. The contact of the neck planer portion 40 and the body planer portion 36 provide for a stable support of the neck component 18 onto the stem component 12.

For simplicity and as shown in FIG. 1, the stem component 12 defines a longitudinal axis 42 of the stem component 12. For simplicity and to provide for strength and rigidity, the neck planer portion 40 and the body planer portion 36 are generally normal or perpendicular to the longitudinal axis 42.

As shown in FIG. 1, the hip stem 10 may include a connector in the form of, for example a fastener, for example a screw 44 to connect the neck component 18 to the stem component 12. As shown in FIG. 1, the connector 44 may be in the form of, for example, a screw. The connector 44 is in contact with both the stem component 12 and the neck component 18.

Neck component 18 may be connected to the stem component 12 in many different ways within the various embodiments of the present invention. For example and as shown in FIG. 1, the distal body portion 22 of the neck component 18 may include a protrusion 46 extending downwardly from the neck planer portion 40. Protrusion 46 may have any suitable shape, and may as shown in FIG. 1 have a generally circular cross-section and be tapered defining an included angle α. Stem component 12 may, in order to receive the protrusion 46 of the neck component 18, define an aperture 48 formed in the proximal body portion 16 of the stem component 12. Aperture 48 may have a contour matching that of the protrusion 46 for receiving the protrusion therein. It should be appreciated that the angle α may be sufficiently small to provide for a soft self-locking feature between the protrusion 46 and the aperture 48.

For a self-locking taper the angle α should be defined by the formula;

$$\text{Tan} \frac{(\alpha/2) < \mu}{2}$$

where µ=coefficient of friction
α=included angle

Referring now to FIG. 1-B, the protrusion 46 and the aperture 48 are shown in cross-section. As shown in FIG. 1-B, the protrusion 46 has a circular cross-section defined by protrusion diameter PD.

As shown in FIG. 1, the connector 44 may be in the form of a screw. The screw 44 may be any suitable screw and may, as shown in FIG. 1, have a flat head and be in the form of a socket-headed cap screw. Connector 44 may be received by the neck component 18 by a connector opening 50 formed in the neck component 18 and positioned about longitudinal axis 42. The connector 44 may be received into the stem component 12 through stem component aperture 52. The stem component aperture 52 may include internal threads 54 that mate with external threads 56 formed on the connector or screw 44.

The hip stem 10 including the stem component 12, the neck component 18 as well as the screw 44 may be made of any suitable durable material. For example, the stem component 12, the neck component 18 and the connector 44 may be made of, for example, a metal, a plastic or a composite. The materials from which the components of the hip stem 10 are manufactured preferably are materials that are compatible with the human body. For example, if the stem component 12, neck component 18, or the connector or screw 44 are made of a metal, the components may be made of, for example, a cobalt chromium alloy, a stainless steel alloy, or a titanium alloy.

The stem component 12 may have any suitable shape capable of insertion into the canal 4 of the femur 6. For example, the stem component 12 may include a stem periphery 58 having a shape similar to that of the broach or rasp used to form the cavity 2 in the canal 4 of the long bone or femur 6. The proximal body portion 16 of the stem component 12 may, as shown in FIG. 1, have a larger cross-section than that of the distal stem portion 14 to conform with the corresponding shape of the natural femur 6.

The neck component 18 of the hip stem 10 may have any suitable shape capable of mating with the stem component 12 and capable of providing support for the ball or head 60 which may be placed on external taper 62 formed on neck 64 of the neck component 18. It should be appreciated that the hip stem 10 may be integral with the neck component 18.

As shown in FIG. 1, hip stem or orthopaedic implant stem 10 is used for performing joint arthroplasty. A portion of the orthopaedic implant stem 10 may be fitted to cavity 2 in the canal 4 of long bone 6. The orthopaedic implant stem 10 includes a stem component or canal element 12 having external stem periphery 58. The canal element 12 has a first end 15 for insertion into the cavity and an opposed connection end 17. The canal element 12 has pocket or recess 32 extending from opposed connection end 17 of the canal element 12. The recess 32 has an internal periphery 23. The recess 32 has a portion that is coaxial with the longitudinal axis 42 of the stem component 12. The canal element 12 also has external periphery 58 spaced outwardly from the internal periphery 23 of the recess 32. The orthopaedic implant stem 10 further includes neck component or body element 18 that may be fixedly connected to the canal element 12. Distal body portion or first distal body portion 22 of the neck component 18 may be inserted into the recess 32 of the canal element when the neck component 18 is fixedly connected to the canal element 12. External periphery 78 of the first portion 22 of the neck component 18 is spaced inwardly from the external periphery 58 of the canal element 12 when the neck component 18 is fixedly connected to the canal element 12 so that the neck component 18 may be removed from the long bone 6 without disturbing the fixation of the canal element 12 to the long bone 6. In other words, the recess 32 of the stem component 12 is sized and shaped to receive first portion 22 of the neck component 18 along the longitudinal axis 42 of the stem component 12.

As shown in FIG. 1, the distal body portion 22 of the neck component 18 may have any suitable shape and typically has a shape compatible for placement within the recess or pocket 32 formed in the proximal body portion 16 of the stem component 12. For example, the distal body portion 22 may, as shown in FIG. 2, have a generally rectangular shape defined by neck body width NBW and neck body length NBL.

Figure 1A:
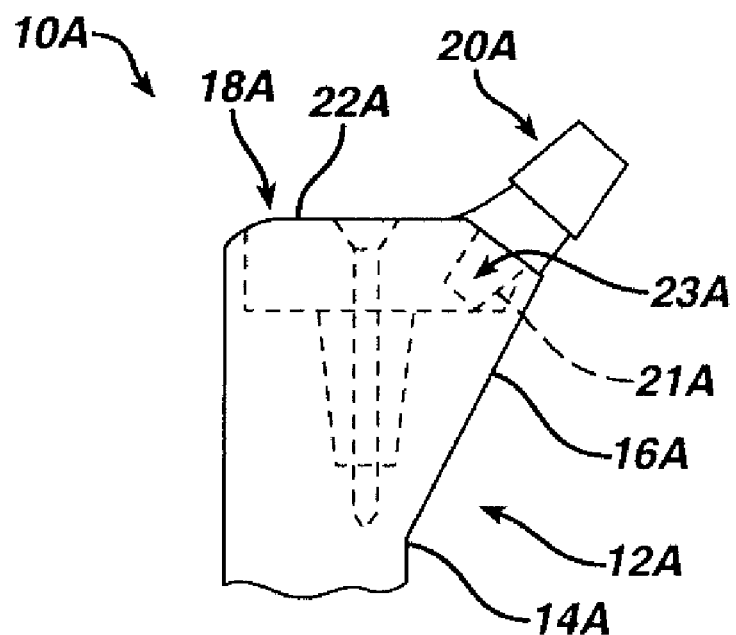
FIG. 1A is a partial plan view of an alternate embodiment of the present invention in the form of a modular hip stem with a tapered stem connection and a modular neck.
Figure 1B:
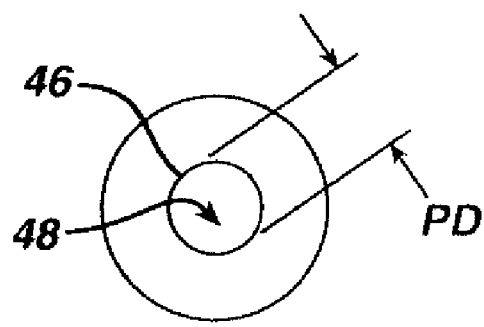
FIG. 1B is a cross-sectional view of FIG. 1 along the line 1B-1B in the direction of the arrows.

Referring now to FIG. 1A, another embodiment of the present invention is shown as hip stem 10A. The hip stem 10A is similar to the hip stem 10 of FIG. 1, except that the neck component 18A is of a modular construction or is made from more than one piece. For example, as shown in FIG. 1A, the neck component 18A includes a distal body component 22A and a proximal neck component 20A. The proximal neck component 20A may be secured to the distal body component 22A in any suitable fashion.

As shown in FIG. 1A, the proximal neck component 20A includes an external taper 21A that mates with a cavity 23A formed in the distal body component 22A. It should be appreciated that the components forming the neck component 18A may be threadably attached, press-fit attached or have a bayonet lock or any type of connector. The hip stem 10A further includes a stem component 12A which is similar to the stem component 12 and includes a distal stem portion 14A and a proximal body portion 16A.

Figure 2:
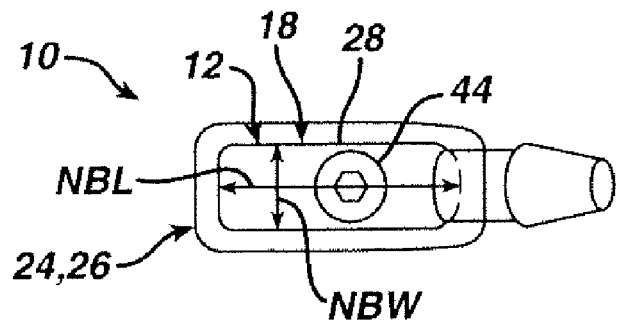
FIG. 2 is a top view of the modular hip stem of FIG. 1.

Hip stem 10 of the present invention, as shown in FIG. 1 and FIG. 2, may be utilized for both cemented and cementless hip arthroplasty. For example, the hip stem 10 may be used with a femur having a cavity prepared for cement with the cement being positioned between the femur 6 and the hip stem 10. The cavity 2 of the femur 6 may alternatively be prepared such that the stem periphery 58 may directly connect with the periphery of the cavity 2. It should be appreciated that whether the hip stem 10 uses cemented or cementless construction, the neck component 18 may be removed from the stem component 12 without disruption of the bone implant ingrowth.

Figure 4:
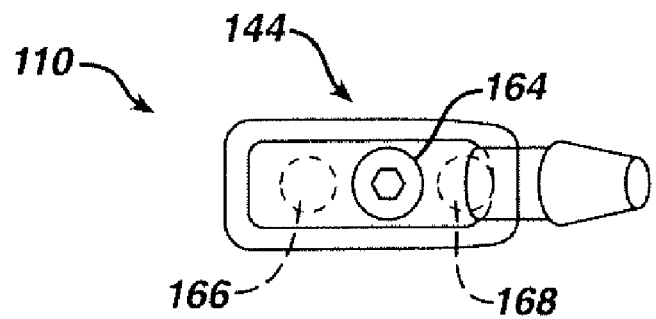
FIG. 4 is a top view of the modular hip stem of FIG. 3.
Figure 3:
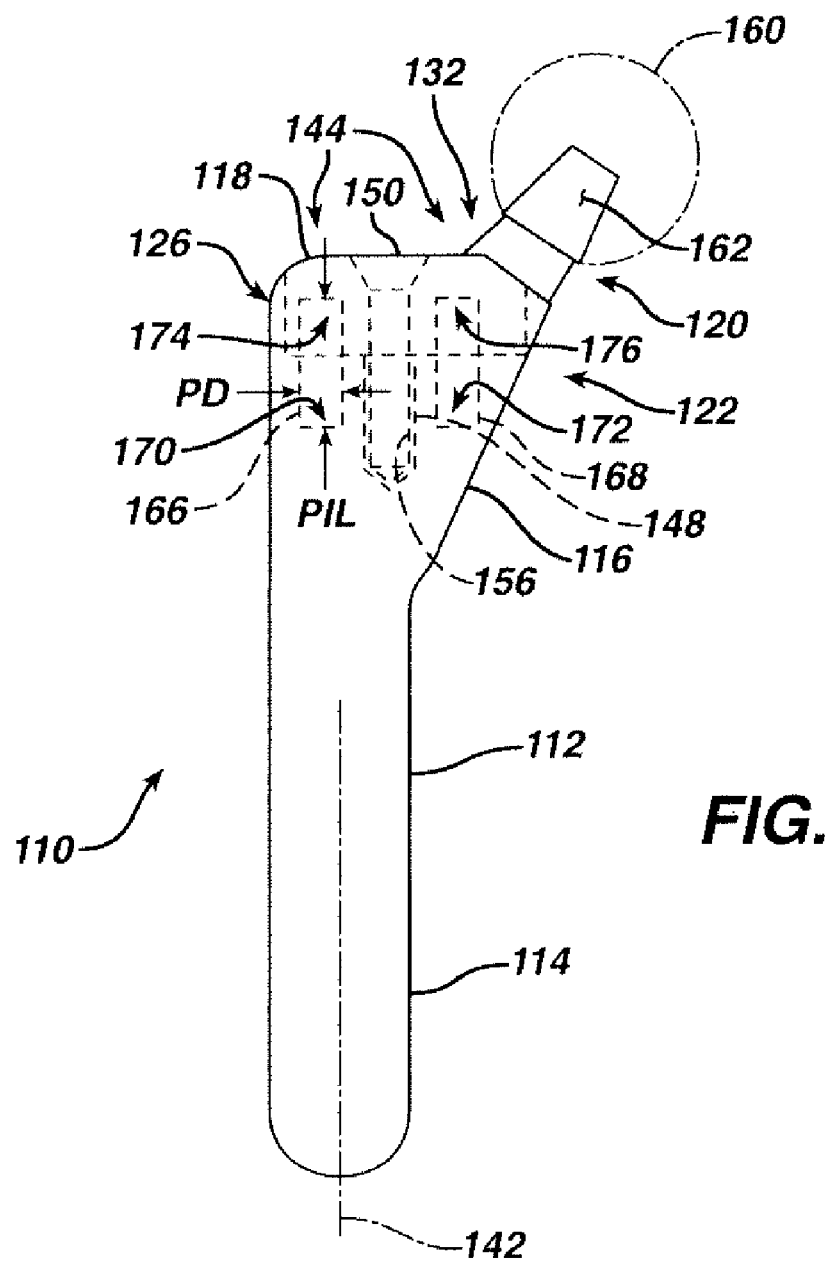
FIG. 3 is a plan view of a modular hip stem in accordance with another embodiment of the present invention utilizing dowel pins and a screw.

According to the present invention and referring now to FIGS. 3 and 4, yet another embodiment of the present invention is shown as hip stem 110. Hip stem 110 is similar to the hip stem 10 of FIGS. 1 and 2 and may, in fact, be made of similar materials with generally similar shapes. The hip stem 110, however, is different from the hip stem 10 of FIGS. 1 and 2.

For example and as shown in FIGS. 3 and 4, the hip stem 110 includes a stem component 112 somewhat similar to the hip stem component 12 of FIGS. 1 and 2. The hip stem 110 further includes a neck component 118 somewhat similar to the neck component 18 of FIGS. 1 and 2. The hip stem 110 further includes a connector 144 which is different than connector 44 of the hip stem 10 of FIGS. 1 and 2.

For example, as shown in FIGS. 3 and 4, the connector 144 includes a screw 164 similar to the screw 44 of the hip stem 10 of FIGS. 1 and 2. In addition to the screw 64, the connector 144 further includes a pin, for example, first pin 166. The hip stem 110, it should be appreciated, may be manufactured with a solitary pin 166 but may, as shown in FIGS. 3 and 4, further include a second pin 168. The pins 166 and 168 as well as the screw 164 serve to form the connector 144. The connector 144 is used to connect the neck component 118 to the stem component 112.

The first pin 166 and the second pin 168 may, for simplicity as shown in FIGS. 3 and 4, be substantially the same. For example, the pins 166 and 168 may be cylindrical. For example, the first pin 166 and the second pin 168 may be defined by a pin diameter PD and a pin length PIL. The first pin 166 and the second pin 168 may be made of any suitable durable material and may, for example, be made of a metal. If made of a metal, the first pin 166 and the second pin 168 may, for example, be made of a material compatible with a human body. For example, a cobalt chromium alloy, a stainless steel alloy, or a titanium alloy.

The stem component 112 may, as is shown in FIGS. 3 and 4, have a distal stem portion 114 and a proximal body portion 116. Internal threads 156 may be formed on proximal body portion 116 to mate with external threads 148 formed on the screw 164. The proximal body portion 116 of the stem component 112 may define a first pin stem opening 170 for receiving the first pin 166 as well as a second pin stem opening 172 for receiving the second pin 168. The pins 166 and 168 may be matingly fitted to the openings 172 and 170. The proximal body portion 116 may further include a sleeve portion 126 which forms a pocket 132 for receiving the neck component 118. The neck component 118 may include a screw opening 150 for receiving the screw 164. The neck component 118 may further define a first pin neck opening 174 for receiving a portion of the first pin 166 as well as a second pin neck opening 176 for receiving the second pin 168.

It should be appreciated that to minimize the number of loose parts the first pin 166 and the second pin 168 may be fixably secured to one of the neck component 118 or the stem component 112. It should be appreciated that the first pin 166 and the second pin 168 would then be slidably secured to the other of the stem component 112 and the neck component 118.

The neck component 118 includes a distal body portion 122 as well as a proximal neck portion 120. The proximal neck portion 120 may define an external taper 162 which matingly receives a ball or head 160.

Figure 3A:
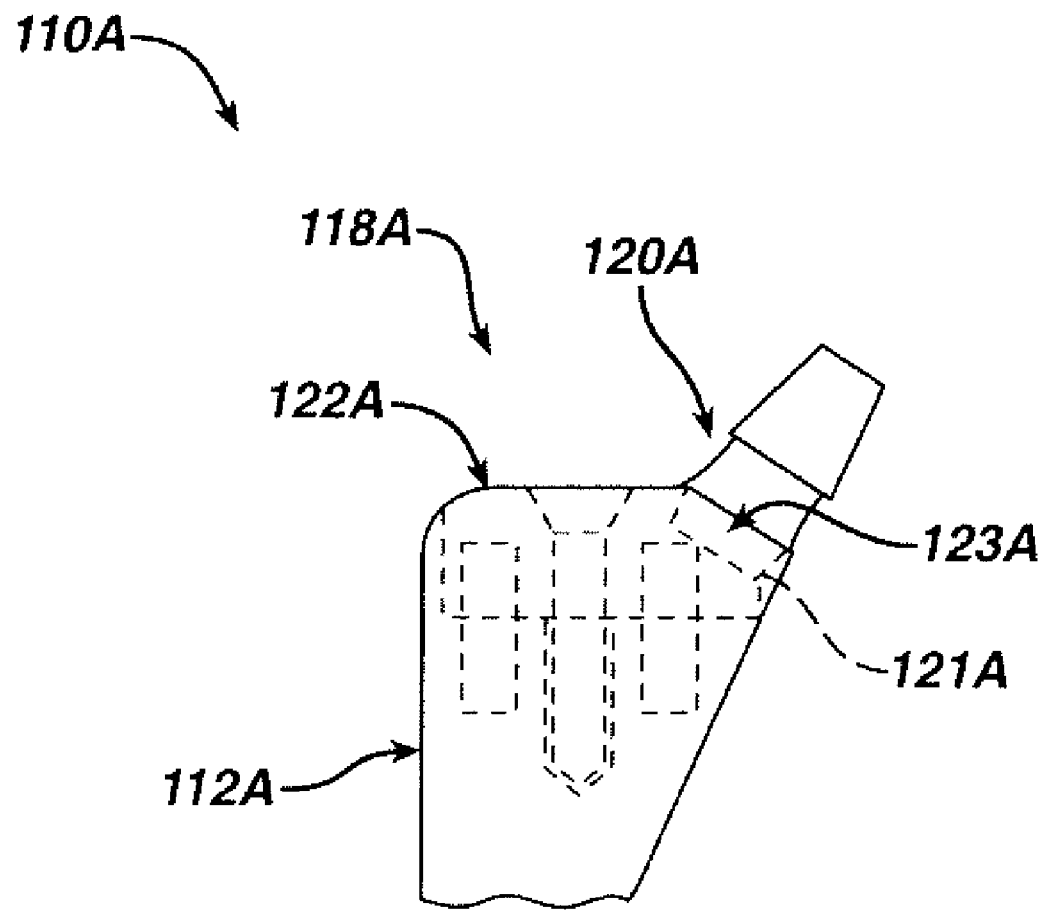
FIG. 3A is a partial plan view of an alternate embodiment of the present invention in the form of a modular hip stem with a pinned stem connection and a modular neck.

Referring now to FIG. 3A, yet another embodiment of the present invention is shown as hip stem 110A. The hip stem 110A is similar to the hip stem 110 of FIGS. 3 and 4, except that the neck component 118A is different than the neck component 118 of the hip stem 110 of FIGS. 3 and 4 in that the neck component 118A is modular or made of more than one component. For example, as shown in FIG. 3A, the neck component 118A includes a distal body component 122A which is connectable to a proximal neck component 120A. It should be appreciated that the distal body component 122A and the proximal neck component 120A may be connected to each other in any suitable fashion, for example they may be threadably connected, have a bayonet connection, have a press-fit connection or, as is shown in FIG. 3A, have a tapered connection. For example, the distal body component 122A may include a tapered cavity 123A for receiving a tapered protrusion 121A extending from the proximal neck component 120A. Hip stem 110A further includes a stem component 112A which together with the neck assembly 118A forms the hip stem 110A.

Figure 5:
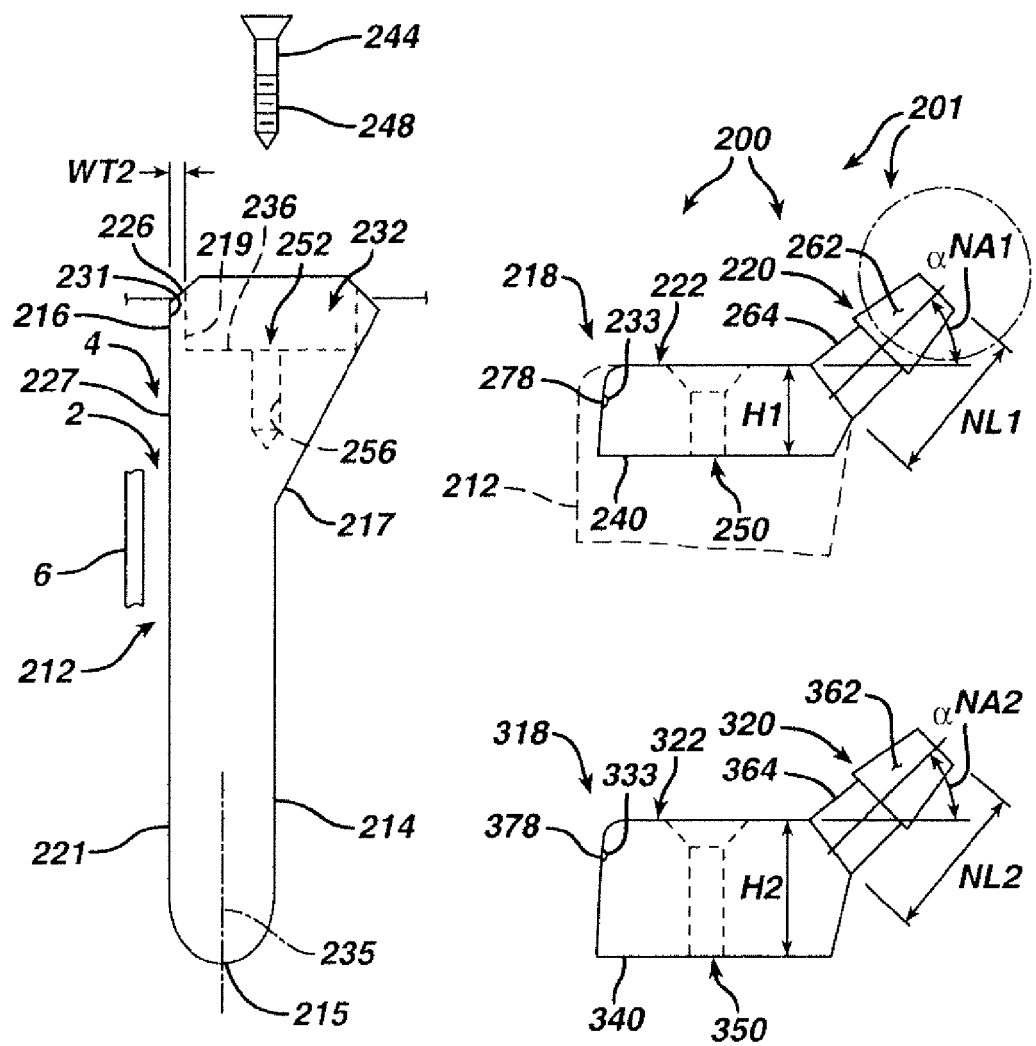
FIG. 5 is a plan view of a kit for performing hip orthopaedic surgery in accordance with yet another embodiment of the present invention.
Figure 6:
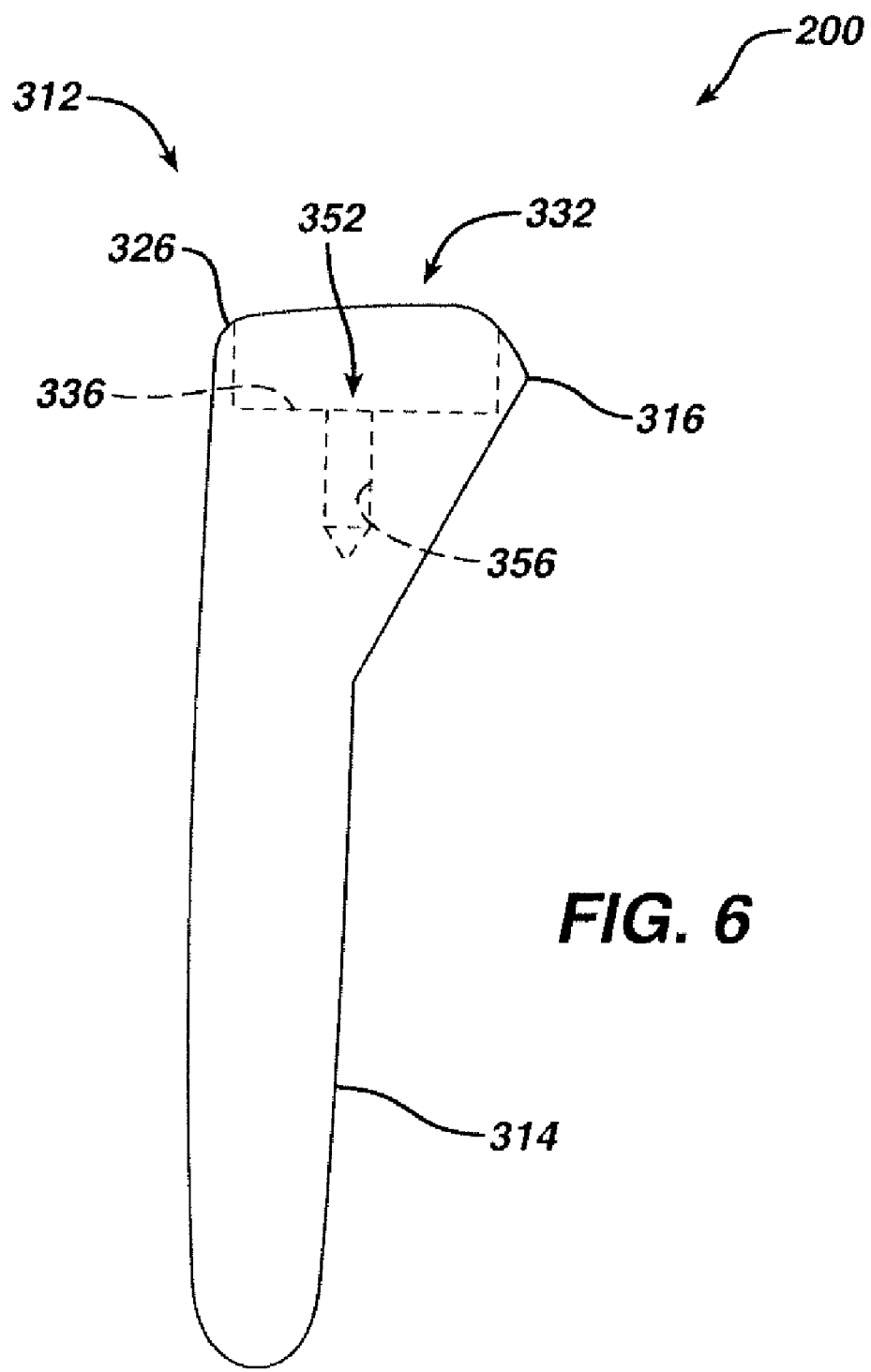
FIG. 6 is a plan view of a second stem component of a modular hip stem for use with the kit of FIG. 5.
Figure 7:
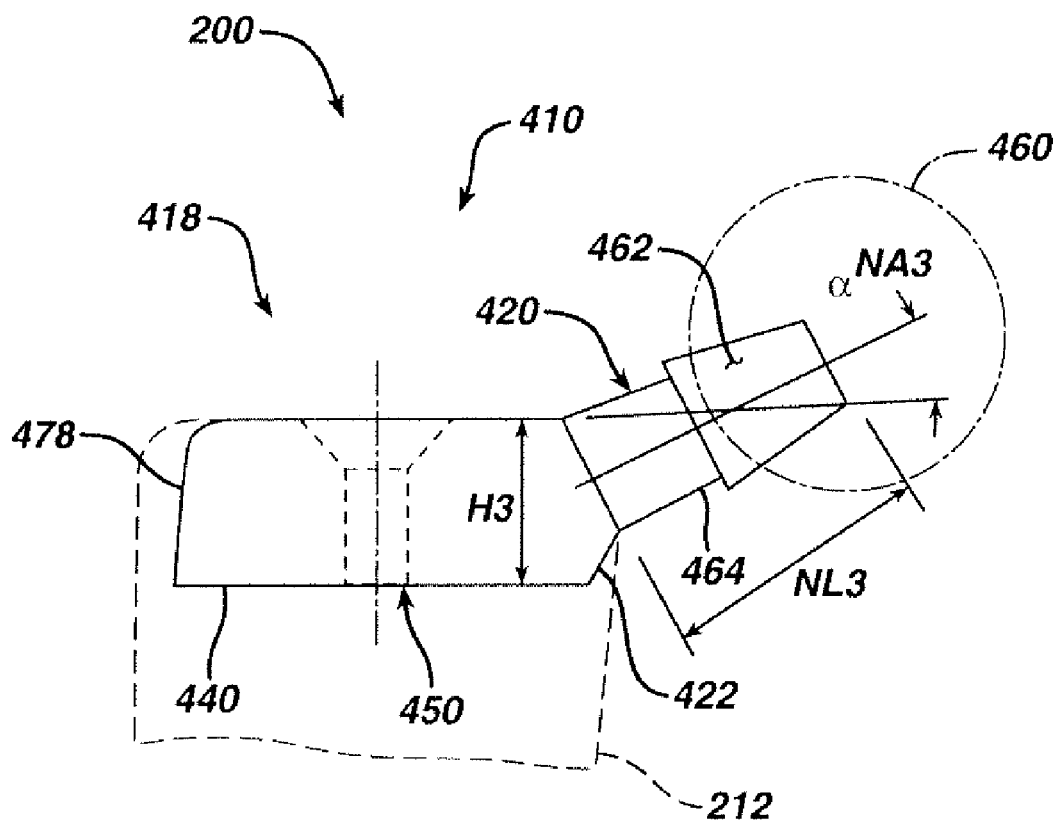
FIG. 7 is a plan view of a neck component of a modular hip stem for use with the kit of FIG. 5 including a through opening for utilizing a screw and having different offsets than the neck components of FIG. 5.

Referring now to FIGS. 5, 6 and 7, yet another embodiment of the present invention is shown as Kit 200. The Kit 200 is for use in performing a primary or a revision arthroplasty. The Kit 200 includes a first stem component 212, a first neck component 218, and a second neck component 318.

The first stem component 212 includes a distal stem portion 214 and a proximal body portion 216. The first stem component 212 may have any suitable shape and may have a shape somewhat similar to the stem component 12 of FIG. 1. As shown in FIG. 5, the first stem component 212 may include a pocket 232 formed by sleeve 226 of the stem 212. The pocket 232 is adapted for receiving the first neck component 218 or, alternatively, the second neck component 318.

As shown in FIG. 5, to secure the neck components 218 and 318 to the first stem component 212, the stem component 212 may include an aperture 252 extending inwardly from planer face 236 of the pocket 232. Internal threads 254 may be formed in aperture 252. The internal threads 254 may cooperate with external threads 256 formed on screw 244.

The first neck component 218 may be similar to the neck component 18 of the hip stem 10 of FIGS. 1 and 2. The first neck component 218, however, does not include a protrusion such as the protrusion 46 of the neck component 18 of FIGS. 1 and 2. First neck component 218 includes a distal body portion 222 and a proximal neck portion 220 extending from the distal body portion 222.

The distal body portion 222 defines a planer face 240 for cooperation with the planer face 236 of the first stem component 212. The distal body portion 222 further defines a periphery 278 which mates with sleeve 226 of the first stem component 212. The distal body portion 222 further defines an opening 250 for receiving the screw 244. The proximal neck portion 220 defines a neck 264 from which extends an external taper 262. A head 260, as shown in phantom, may be fitted onto the external taper 262.

The first neck component 218 defines a height H1, a neck length NL1 and a neck angle α NA1. The combination of neck height, length, and angle assist in positioning the head 260 with respect to the stem 212. Unique patient anatomies require that the head 260 be put in the proper position. By utilizing the kit 200 of the present invention, various neck components can be utilized to provide for variations in the position of the head.

For example, and as shown in FIG. 5, the kit 200 further includes a second neck component 318. The second neck component 318 includes different dimensions than the first neck component 218 so that the head may be positioned in a different location than that obtained if the first neck component 218 is used.

For example, and as shown in FIG. 5, the second neck component 318 includes a distal body portion 322 and a proximal neck portion 320. Distal body portion 322 includes a planer face 340 for cooperation with the planer face 236 of the stem 212. The distal body portion 322 further defines a periphery 378 for mating with sleeve 226 of the stem 214. The distal body portion 322 defines an opening 350 receiving the screw 244.

The proximal neck portion 320 defines a neck 364 which is connected to the distal body portion 322. An external taper 362 extends from the neck 364. As shown in FIG. 5, the periphery 366 of the distal body portion 322 and the planer face 340, as well as the opening 350 of the second neck component 318 have configurations compatible with the planer face 340, the opening 350, and the periphery 266 of the distal body portion 322 of the first neck component 218 in order that the first neck component 218 and the second neck component 318 may be selectively used with the first stem component 212.

As shown in FIG. 5, the second neck component 318 may include a height H2 which is different than the height H1 of the first neck component 218. Similarly, the proximal neck portion 320 of the second neck component 318 may define a neck length NL2 which is different than neck length NL1 of the proximal neck portion 220 of the first neck component 218. Further, the proximal neck portion of the second neck component 318 may define a neck angle α NA2 which is different than the neck angle α NA1 of the proximal neck portion 220 of the first neck component 218. It should be appreciated that different neck components may be accomplished where only one of the neck height, neck length, and neck angle are different from each other.

Referring again to FIG. 5 and according to the present invention a kit 201 for use in performing revision surgery on the cavity 2 in the canal 4 of the long bone 6 is shown. The cavity 2 extends from a resected plane 11 of the long bone 6. The kit 20 includes first stem component or canal component 212 having an external periphery 221. A portion of the canal component 212 may be fitted to the cavity 2 in the canal 4 of the long bone 6. The canal component 212 includes distal stem portion or canal portion 214 having a first end 215 for insertion into the cavity and an opposed second end 217. The canal component 212 further includes a sleeve portion 226 extending from the second end 217 of the canal portion 212. The sleeve portion 226 has an internal periphery 219 defining pocket or internal cavity 232. The sleeve portion 226 also has an external periphery 227. The kit 201 also includes first neck component or first joint component 218 removably connectable to the canal component 212. The first joint component 218 has a proximal neck portion or body portion 220 and a distal body portion or connection portion 222. The connection portion 222 of the first joint component 218 has an external periphery 278. A portion of the external periphery 278 of the connection portion 222 of the first joint component 218 may be fitted into the internal cavity 232 of the sleeve portion 226 of the canal component 212.

The kit 201 also includes a second neck component or a second joint component 318 that is removably connectable to the canal component 212. The second joint component 318 has a proximal neck portion or body portion 320 and distal body portion or connection portion 322. The connection portion 322 of the second joint component 318 has an external periphery 378. A portion of the external periphery 378 of the connection portion 322 of the second joint component 318 is fitted into the internal cavity 232 of the sleeve portion 226 of the canal component 212 so that the external periphery 378 of the connection portion 322 of the first joint component 218 is spaced inwardly from the external periphery 227 of the sleeve portion 226 of the canal component 212 when the first joint component 218 is fixedly connected to the canal component 212 so that the first joint component 218 may be removed from the long bone 6 and replaced with the second joint component 318 without disturbing the fixation of the canal component 212 to the long bone 6.

The kit 201 may, as shown in FIG. 5, be configured such that the canal component 212, the first joint component 218, and/or the second joint component 318 define resection rings 231, 233 and 333, respectively, on a surface of the component. The resection rings 231, 233 and 333 may be used to align the component axially with the resection plane 11.

The first resection ring 231 as shown in FIG. 5 may be visually distinguishable from the exterior periphery or surface 227 of the canal component 212 adjacent to the ring 231. It should be appreciated that any or all of the resection rings 231, 233 and 333 may be invisible.

The kit 201, may as shown in FIG. 5, be configured such that a portion of the canal component 212 is extendable over a portion of at least one of the first joint component 218 or the second joint component 318.

The kit 201 may, as shown in FIG. 5, be configured such that the first joint component 218 and the second joint component 318 have at least one dimension that is different from each other.

The kit 201 may, as shown in FIG. 5, be configured such that a portion 236 of the external periphery 227 of the canal component 212 is generally planar. Further a portion 240 of the external periphery 278 of the connection portion 222 of the first joint component 218 may, as shown, be generally planar. The portion 236 of the external periphery 227 of the canal component 212 and the portion 240 of the external periphery 278 of the connection portion 222 of the first joint component 218 may, as shown, contact each other.

Figure 13:
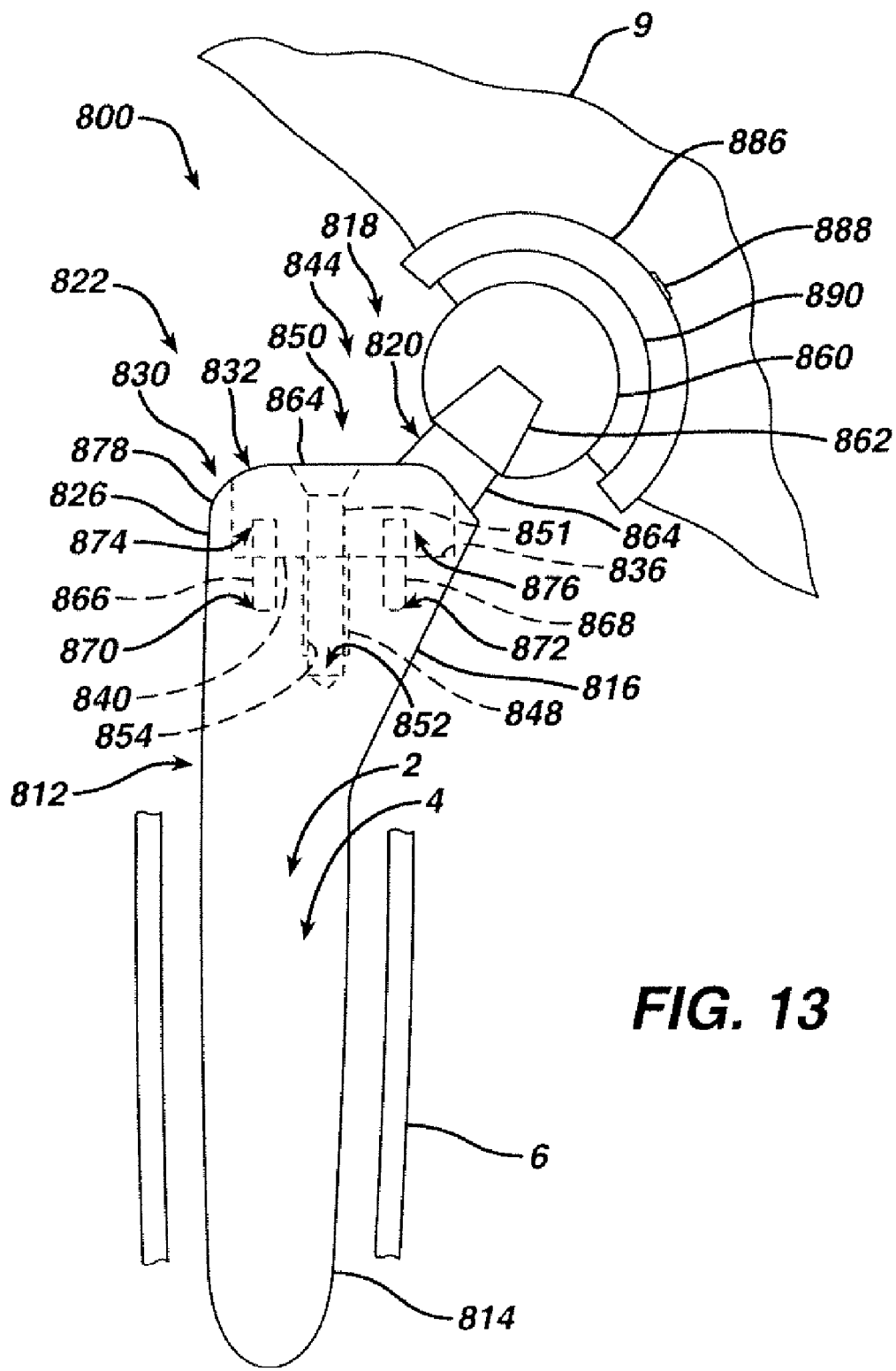
FIG. 13 is a plan view of a hip implant in accordance to another embodiment of the present invention including a modular hip stem similar to that of FIG. 3.

The kit 201 may, as shown in FIG. 5, also include a connector 244 to connect the joint component 218 to the canal component 212. For example, the connector 244 may be in the form of a screw or as shown in FIG. 13 as a pin.

The kit 201 may alternately (see FIG. 1) be constructed such that the first joint component 218 may include a protrusion. To cooperate with the protrusion, the canal component 212 may define an aperture for receiving the protrusion. The protrusion and the aperture may have any suitable shape and may, for example, be cylindrical or tapered.

It should be appreciated that the canal component 212 may alternately include a protrusion (not shown). The first joint component 218 may then include an aperture for receiving the protrusion.

The kit 201 may (see FIG. 16) further include a prosthetic component adapted for implantation to a second bone. The prosthetic component may cooperate with the first joint component 218. Further at least a portion of the body portion 220 of the first joint component 218 may include an articulation surface for articulation with the prosthetic component.

The kit 201 may also include a prosthetic component for fixed implantation to a second bone and for cooperation with the first joint component. The kit 201 may also include a bearing component positionable between the first joint component and the prosthetic component. The bearing component may articulate with the first joint component and/or the prosthetic component.

As shown in FIG. 5, the first joint component 218 may be in the form of, for example, a hip neck. The canal component 212 may correspondingly be in the form of a hip stem. Further the kit may include hip head 260 for attachment to the hip neck 218 and an acetabular cup (see FIG. 16) for articulating cooperation with the hip head 260.

Referring again to FIG. 5, the canal component 212 may define a longitudinal axis 235 and the internal periphery 219 and the external periphery 227 of the sleeve portion of the canal component may also define a wall thickness WT2 therebetween. The wall thickness WT2 may, as shown, be generally uniform in a plane normal to the longitudinal axis 235 of the canal component 212. The external periphery 278 of the connection portion 222 of the first joint component 218 may be adapted to closely conform to the internal periphery 219 of the sleeve portion 226 of the canal component 212.

The canal component 212 may (see FIG. 18) be in the form of a humeral stem and the first joint component 218 may be in the form of a humeral neck. The kit 201 may also include a humeral head for connection with the humeral neck.

Referring now to FIG. 5 the kit may also include connector 244 to connect at the first joint component 218 or the second joint component 318 to the canal component 212. The connector may be in the form of a screw or a pin (See FIG. 16).

As shown in FIG. 6, the kit 200 may further include a second stem component 312. The second stem component 312 may be different than the first stem component 212 and may include a distal stem portion 314 that is longer, has a different angle, is narrower, or is larger or smaller in diameter than the distal stem portion 214 of the first stem component 212.

As shown in FIG. 6, the second component 312 may define a pocket 332 which has generally the same size and shape as the pocket 232 of the first stem component 212 such that either the first neck component 218 or second neck component 318 may be compatible with the second stem component 312 as well as with the first stem component 212. For example, the pocket 332 may be defined by the sleeve 326 extending from planer surface 336. The second stem component 312 may include a proximal body portion 316 that defines an aperture 352 defining internal threads 356 which mate with external threads 256 of the screw 244.

Referring now to FIG. 7, the Kit 200 may further include a third neck component 418. The third neck component 418 includes a distal body portion 422 and a proximal body portion 420. The distal body portion 422 of the third neck component 418 may define planer surface 440 and periphery 478. The surface 440 and periphery 478 which as shown in FIG. 7 are selected such that the third neck component 418 may be compatible and fit in the pocket 232 of the first stem 212.

The distal body portion 422 defines an opening 450 for receiving the screw 244. The proximal neck portion 420 defines a neck 464 extending from the distal body portion 422 and an external taper 462 that extends from the neck 464 and that is adapted for cooperation with a ball or head, for example head 460. It should be appreciated that the external taper 462, of third neck component 418 the external taper 362 of the second neck component 318, as well as the external taper 262 of the first neck component 218 may have similar sizes and shapes, such that the same head or similar heads may be accommodated by all of the associated tapers of the associated neck components.

As shown in FIG. 7 the third neck component 418 defines a neck length NL3, a neck angle α NA3, and a neck height H3. It should be appreciated that at least one of the neck height H3, the neck length NL3 or the neck angle α NA3 may be different than the corresponding dimension for the first neck component 218 or the second neck component 318.

Figure 8:
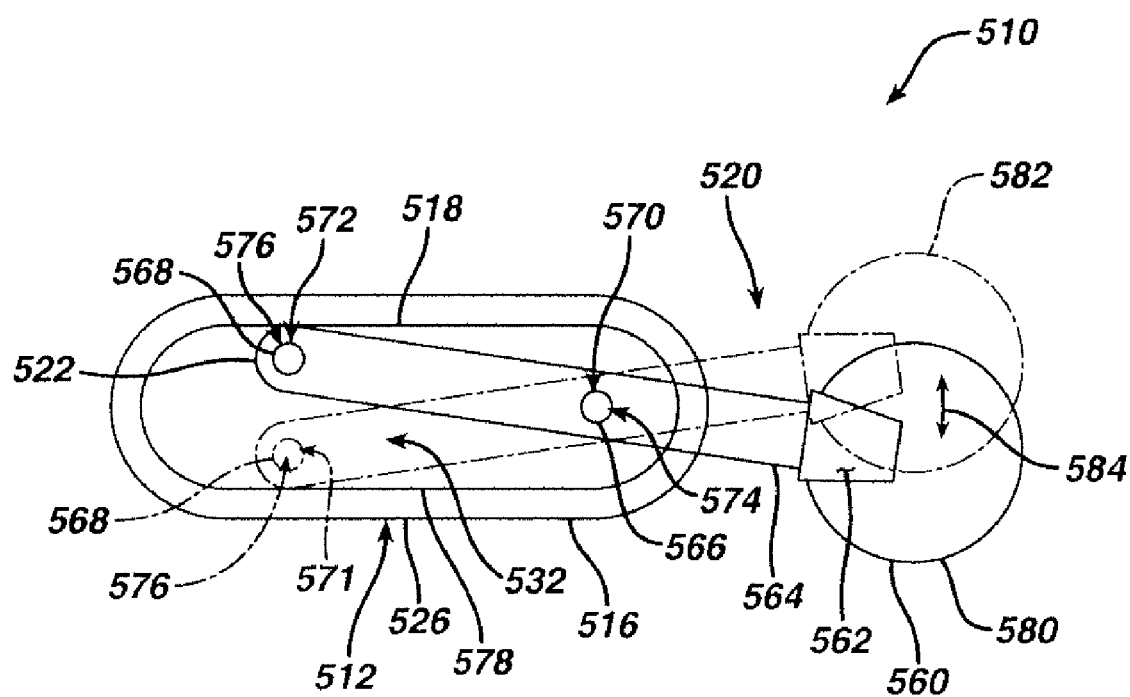
FIG. 8 is a plan view of a modular hip stem in accordance with another embodiment of the present invention utilizing dowel pins to provide for different version with the same stem.

Referring now to FIG. 8, yet another embodiment of the present invention is shown as hip stem 510. The hip stem 510 is different than the hip stem 110 of FIGS. 1 and 2 in that the hip stem 510 provides for two assembly positions. For example, as shown in FIG. 8, hip stem 510 may include an anterior assembly position 580 as is shown in solid and a posterior assembly position 582 as is shown in phantom.

It should be appreciated that as is shown in FIG. 8, the hip stem 510 may be a right hip stem. It should be appreciated that for a left hip stem, the anterior assembly position and the posterior assembly position would be reversed.

According to the present invention, and as shown in FIG. 8, the hip stem 510 includes a stem component 512 as well as a neck component 518. The stem component 512 may be similar to the stem component 12 of FIGS. 1 and 2, except that the stem component 512 includes a plurality of mounting positions for mounting the neck component 518 onto the stem component 512 in a plurality of positions. For example, as shown in FIG. 8, the stem component 518 includes a first stem opening 570 for cooperating with first pin 566.

The stem component 512 further includes a second pin stem anterior opening 571 for receiving the second pin 568. When the second pin 568 is positioned in the second pin stem anterior opening 571, the neck component 518 is positioned with respect to the stem component 512 such that the hip stem 510 is in the posterior assembly position 582 as shown in phantom.

The stem component 512 further includes a second pin stem posterior opening 572. The second pin stem posterior opening 572 is adapted for likewise receiving the second pin 568. When the second pin 568 is positioned in the second pin stem posterior opening 572, the neck component 518 is aligned with the stem component 512 such that the hip stem 510 is assembled into the anterior assembly position 580 is shown in solid.

Proximal body portion 516 of the stem component 512 includes a sleeve portion 526 for cooperation with bone and or cement.

The neck component 518 includes a distal body portion 522 defining a periphery 578 thereof. The periphery 578 of the distal body portion 522 is fitted within cavity or pocket 532 formed in the stem component 512 by the sleeve portion 526. The distal body portion 522 of the neck component 518 includes a first pin neck opening 574 as well as a second pin neck opening 576. The first pin neck opening 574 cooperates with the first pin 566 while the second pin neck opening 576 cooperates with the second pin 568.

A neck 564 extends from the distal body portion 522 of the neck component 518. An exterior taper 562 extends from the neck 564 and serves to receive head 560. The neck 564 and exterior taper 562 form the proximal neck portion 520 of the neck component 518. As can be seen by simply rotating the component 518 after removing the second pin 568 from the stem component 512, the neck component 518 may be rotated about first pin 566 in the direction of arrows 584 to either anterior assembly position 580 or posterior assembly position 582.

Figure 10:
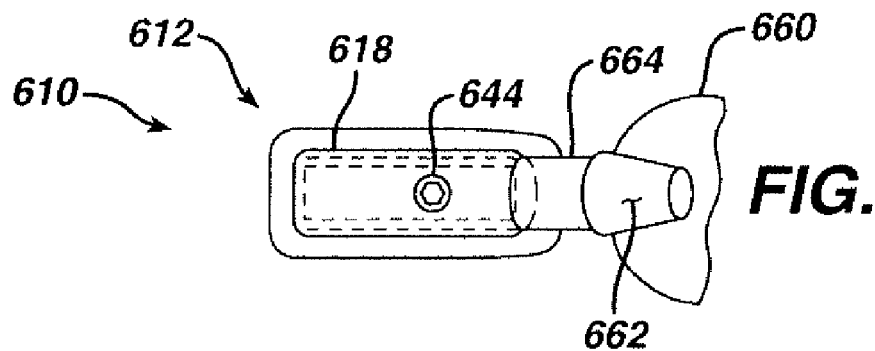
FIG. 10 is a top view of the modular hip stem of FIG. 9.
Figure 9:
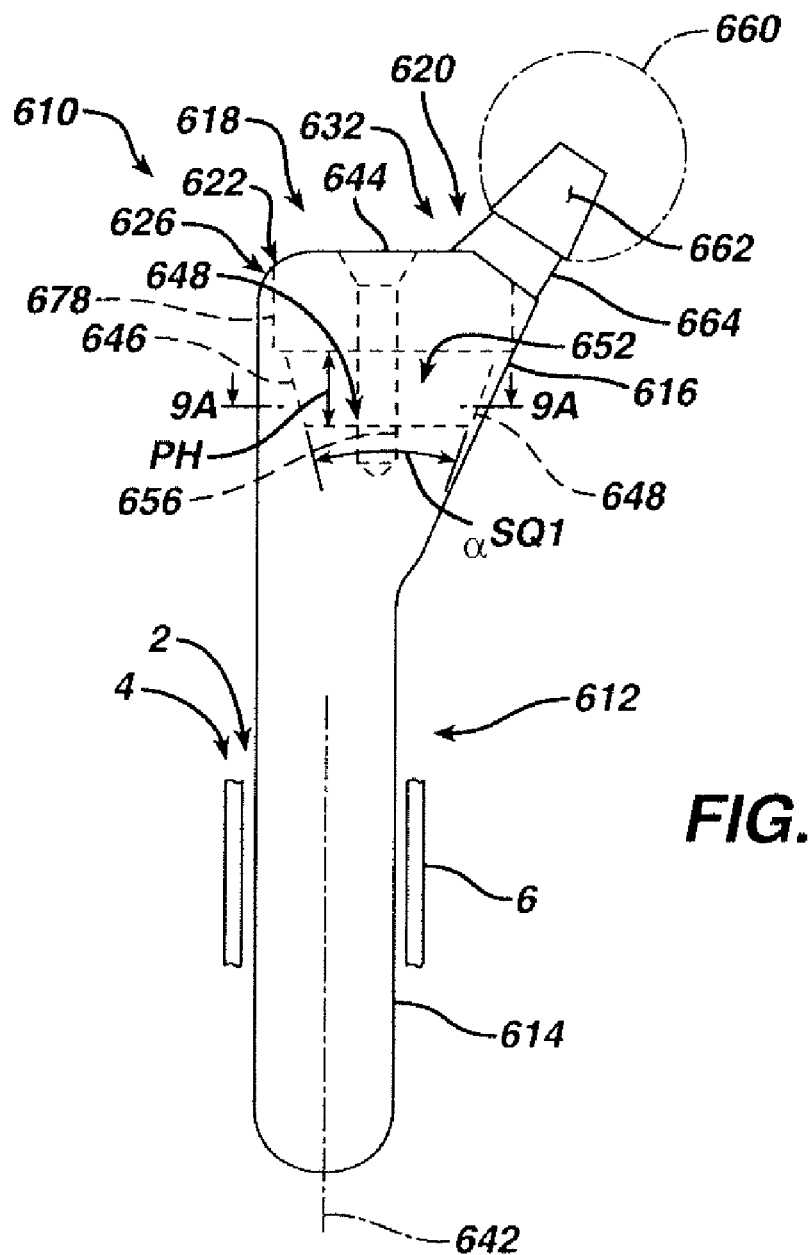
FIG. 9 is a plan view of a modular hip stem in accordance with yet another embodiment of the present invention utilizing a rectangular tapered lock and a screw.
Figure 9A:
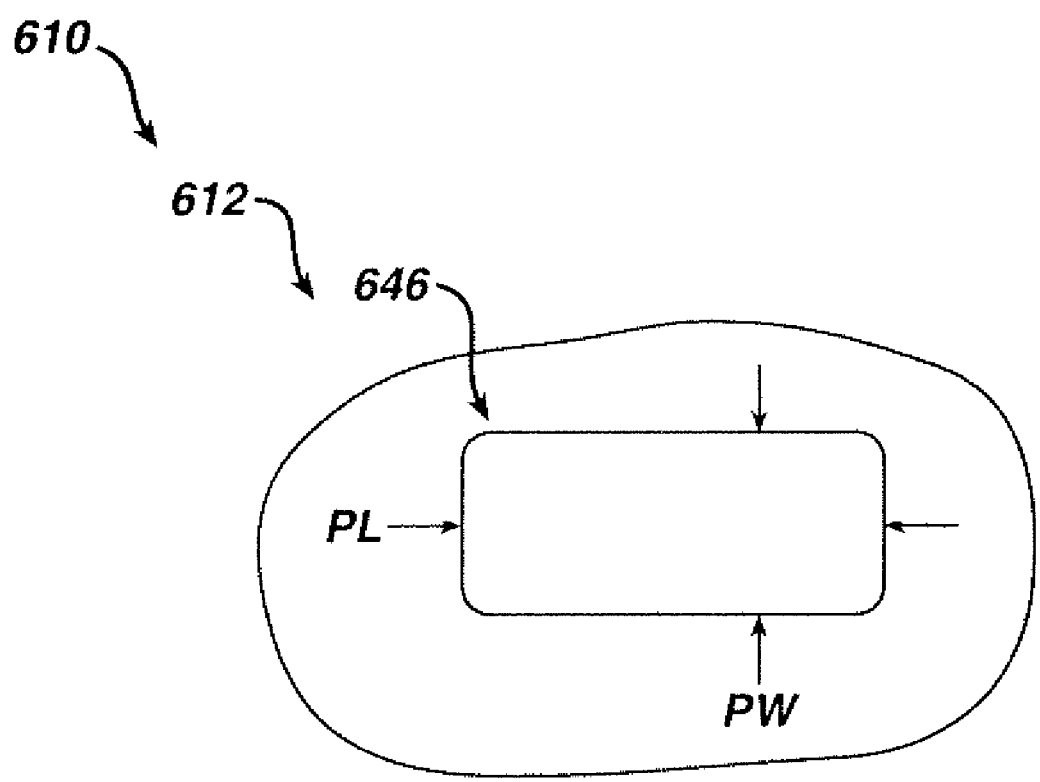
FIG. 9A is a cross-sectional view of FIG. 9 along the line 9A-9A in the direction of the arrows.
Figure 11:
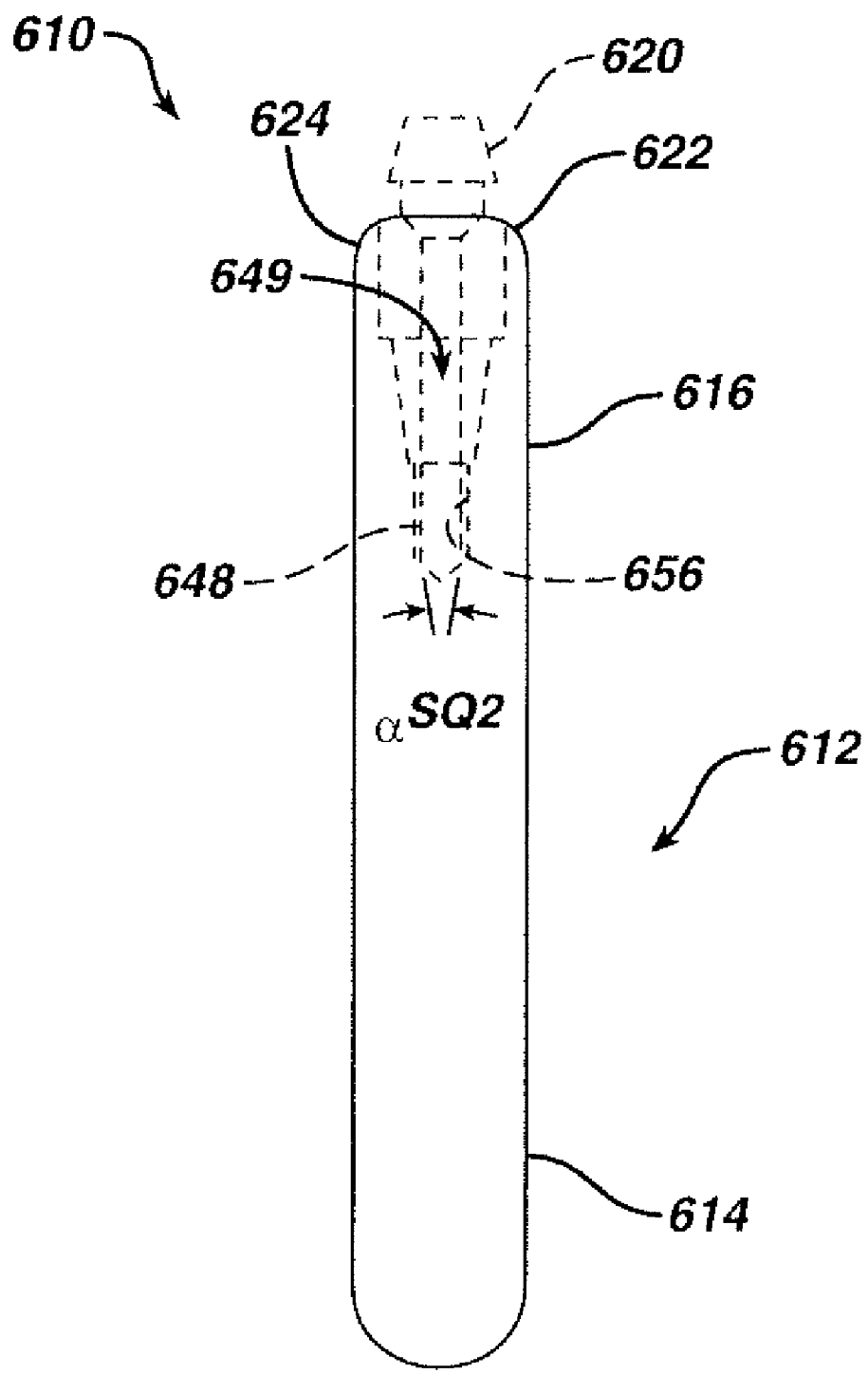
FIG. 11 is an end view of the modular hip stem of FIG. 9.

Referring now to FIGS. 9 and 10, yet another embodiment of the present invention is shown as hip stem 610. The hip stem 610 of FIGS. 9, 10 and 11 is different than the hip stem 10 of FIGS. 1 and 2 in that the hip stem 610 includes an external protrusion 646, which is different than the external protrusion 46 of the hip stem 10 in that the external protrusion 646 is rectangular rather than circular in cross-section. For example, and as shown in FIG. 9, the hip stem 610 includes a stem component 612 as well as a neck component 618.

The stem component 612 includes a distal stem portion 614 for cooperation with the cavity 2 formed in the canal 4 of the femur 6. The stem component further includes a proximal body portion 616 which defines a pocket 632 for receiving the neck component 618. An opening 652 formed in the pocket 632 includes internal threads 656 for cooperation with external threads 648 formed on the screw 644. The proximal body portion 616 of stem component 612 includes an aperture 648 formed therein for receiving the external protrusions 646 extending from neck component 618.

Referring now to FIG. 9-A, the external protrusion 646 and the aperture 648 are shown in cross-section. The aperture 648 and the external protrusion 646 are defined by a protrusion width PW and a protrusion length PL which defines a generally rectangular cross-section of the external protrusion 646, and correspondingly the aperture 648.

Referring again to FIG. 9, the external protrusion 646 further defines a protrusion height PH extending along longitudinal axis 642 of the hip stem 610.

Referring to FIGS. 10 and 11, the neck component 618 includes a distal body portion 622 and a proximal neck portion 620 extending from the distal body portion 622. Stem component 612 includes a sleeve portion 624 which defines a pocket 632 for receiving periphery 678 of the distal body portion 622 of the neck component 618. The neck component 618 includes the distal body portion 622 and the proximal neck portion 620. The proximal neck portion 620 includes a neck 664 and an external taper 662 extending from the neck 664. A head 660 may mate with external taper 662.

The external protrusion 646 may, as shown in FIGS. 10 and 11, be tapered and define first included angle α SQ1 and second included angle αSQ2

Figure 12:
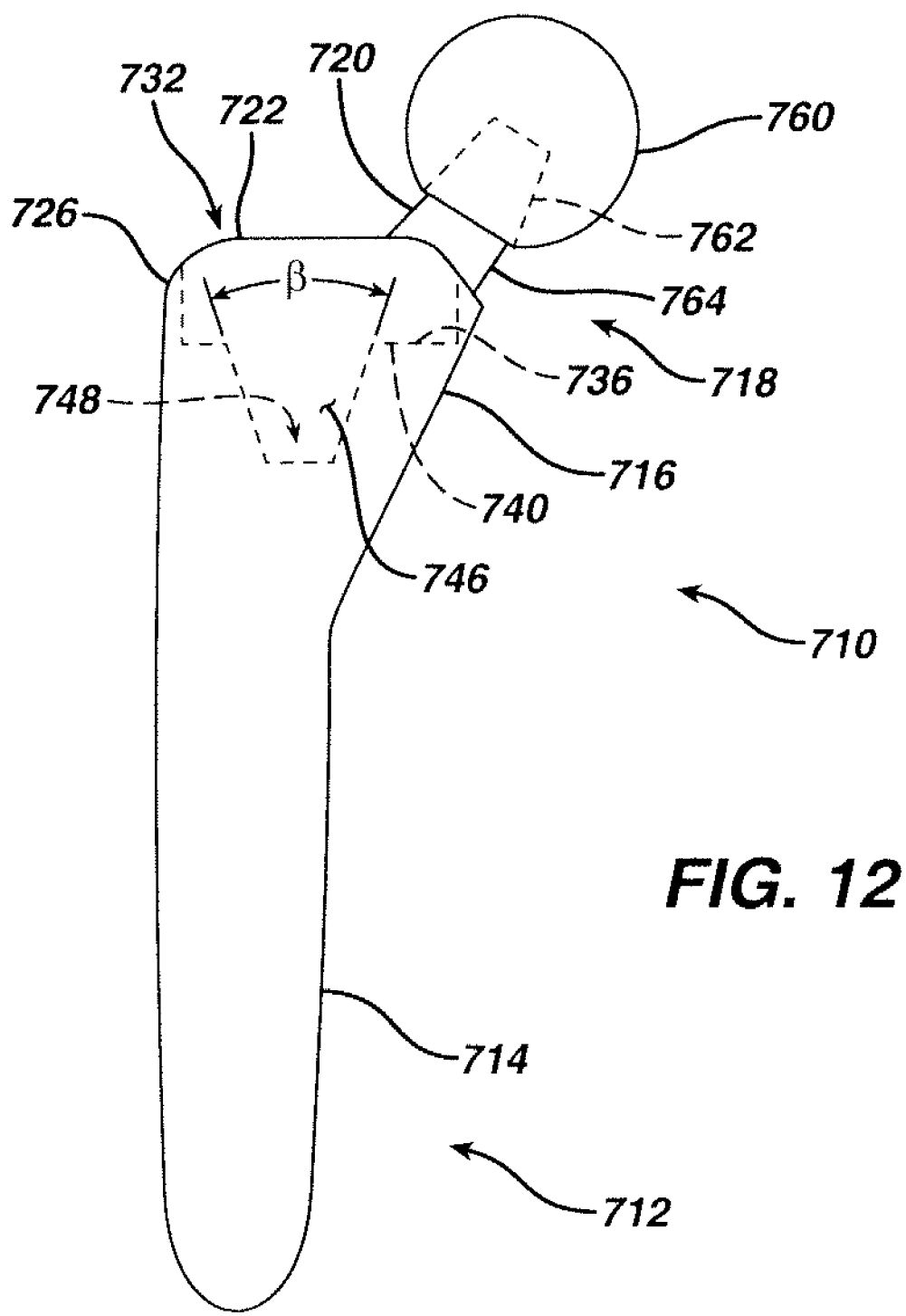
FIG. 12 is a plan view of a modular hip stem in accordance with a further embodiment of the present invention utilizing a tapered lock.

Referring now to FIG. 12, another embodiment of the present invention is shown as hip stem 710. The hip stem 710 is different than the hip stem 10 of FIGS. 1 and 2 in that the hip stem 710 relies solely on a self-locking tapered connection to combine the components of the hip stem 710.

For example, and as shown in FIG. 12, the hip stem 710 includes a stem component 712 as well as a neck component 718. The stem component 712 includes a distal stem portion 714 and a proximal body portion 716. The proximal body portion 716 defines a planer surface 736 from which a cavity 748 extends.

The neck component 718 includes a distal body portion 722 and a proximal neck portion 720 extending from the distal body portion 722. The distal body portion 722 includes a protrusion 746 extending from planer surface 740 of the distal body portion 722.

The protrusion 746 is tapered and defines an included angle β of, for example, two to twenty degrees (2°-20°) for a self locking taper, the angle β is defined by equation:

$$\tan \beta/2 < \mu$$

Where: μ=coefficient of friction
β=included angle

The protrusion 746 cooperates with the cavity 748 to lock the neck component 718 to the stem component 712.

The distal body portion 722 fits within pockets 732 formed by the sleeve portion 726 of the proximal body portion 716 of the stem component 712.

The proximal neck portion 720 includes neck 764 from which external taper 762 extends. The head 760 is fitted onto external taper 762.

According to the present invention and referring now to FIG. 13, yet another embodiment of the present invention is shown as prosthesis 800. The prosthesis 800 as shown in FIG. 13 is in the form of a hip prosthesis. The prosthesis 800 includes a hip stem 810. The hip stem 810 is similar to the hip stem 110 of FIGS. 3 and 4. The hip stem 810 includes a stem component 812 as well as a neck component 818.

The stem component 812 may be similar to the stem component 112 of FIGS. 3 and 4. The stem component 812 includes a distal stem portion 814 adapted to fit within cavity 2 of the canal 4 of femur 6. The stem component further includes a proximal body portion 816 extending from the distal stem portion 814 of the stem component 812. The proximal body portion 816 includes an aperture 852 extending inwardly from inner face 836 of the proximal body portion 816 of the stem component 812. Internal threads 854 are formed in the aperture 852. The internal threads 854 cooperate with external threads 848 formed on screw 851.

The neck component 818 is, as is shown in FIG. 13, connected to the stem component 814 by any suitable connector, for example, by connector 844. The connector 844, as is shown in FIG. 13 includes the screw 851, as well as, a first pin 866. The connector 844 may further include a second pin 868 spaced from and parallel to the first pin 866.

The neck component 818 includes a distal body portion 822 and a proximal neck portion 820 extending from the distal body portion 822. The distal body portion 822 includes an aperture 850 for receiving the screw 851. The distal body portion 822 further includes a first pin neck opening 874 for cooperating with the first pin 866 and a second pin neck opening 876 for cooperating with the second pin 868. The distal body portion 822 further defines a planar face 840 for cooperation with a planar face 836 of the stem component 812.

The proximal body portion 816 of the stem component 812 includes a first pin stem opening 870 for cooperation with the first pin 866 and a second pin stem opening 872 for cooperation with the second pin 868. The proximal body portion 816 of the stem component 812 includes a sleeve portion 826 defining a pocket 832 for receiving periphery 878 of the distal body portion 822 of the neck component 818.

The proximal neck portion 820 of the neck component 818 includes a neck 864 as well as external taper 862 extending from the neck 864.

In addition to the hip stem 810, the prosthesis 800 further includes a head 860 which matingly fits on external taper 862 of the neck component 818. The prosthesis 800 further includes an acetabular cup 886 for cooperation with acetabulum 9 of the patient. The acetabular cup 886 may include a feature in the form of, for example, a porous coated surface 888 for promoting boney in-growth between the acetabulum 9 and the acetabular cup 886. The prosthesis 800 may include a bearing 890 positioned between the acetabular cup 886 and the head 860. It should be appreciated that the acetabular cup 886 may directly cooperate with the head 860.

It should be appreciated that the hip stem 810, head 860, acetabular cup 886, and bearing 890 may be made of any suitable durable material. The hip stem 810 including the distal stem portion 814, the neck component 818, as well as pins 866 and 868 and the screw 864, may all be made of a suitable durable material. The materials for the components of the prosthesis 800 may, for example, be made of a plastic, a metal, or a composite. The material for which the prosthesis is made preferably is compatible with the human anatomy. The prosthesis 800, if made of a metal may for example be made of a cobalt chromium alloy, a stainless steel alloy, or a titanium alloy.

The bearing 890 of the prosthesis 800 may for example, be made of a metal, a ceramic, or a plastic. The head 860 may be made of a metal, or a ceramic.

Figure 14:
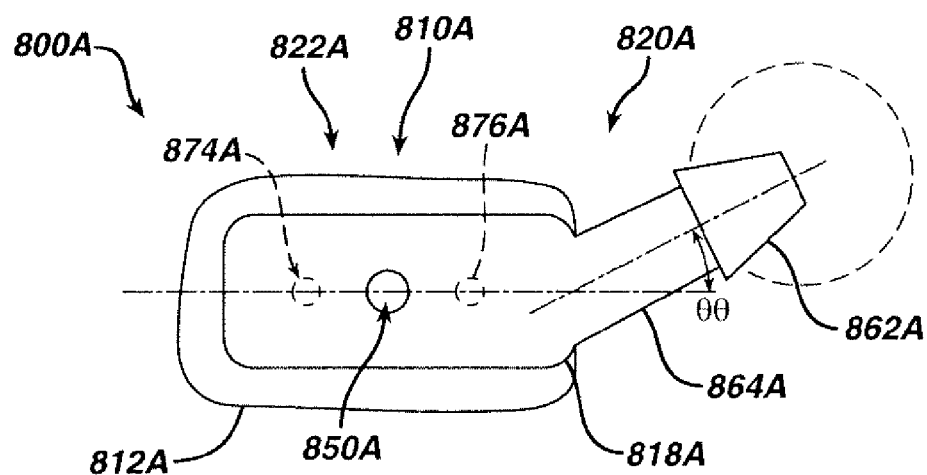
FIG. 14 is a top view of a modular hip stem with left handed proximal component with a neck extending posteriorly and a distal component.
Figure 15:
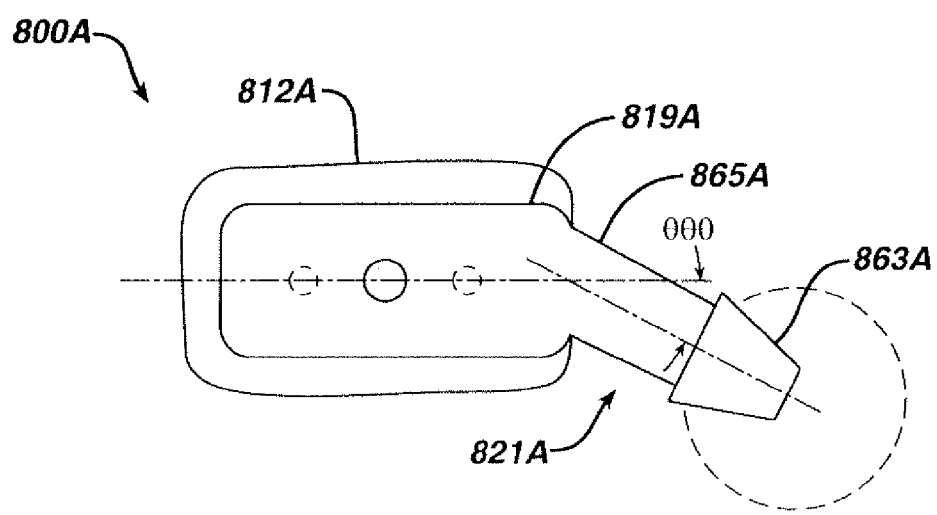
FIG. 15 is a top view of a modular hip stem with a right handed proximal component with a neck extending posteriorly, utilizing the distal component of the hip stem of FIG. 14.
Figure 16:
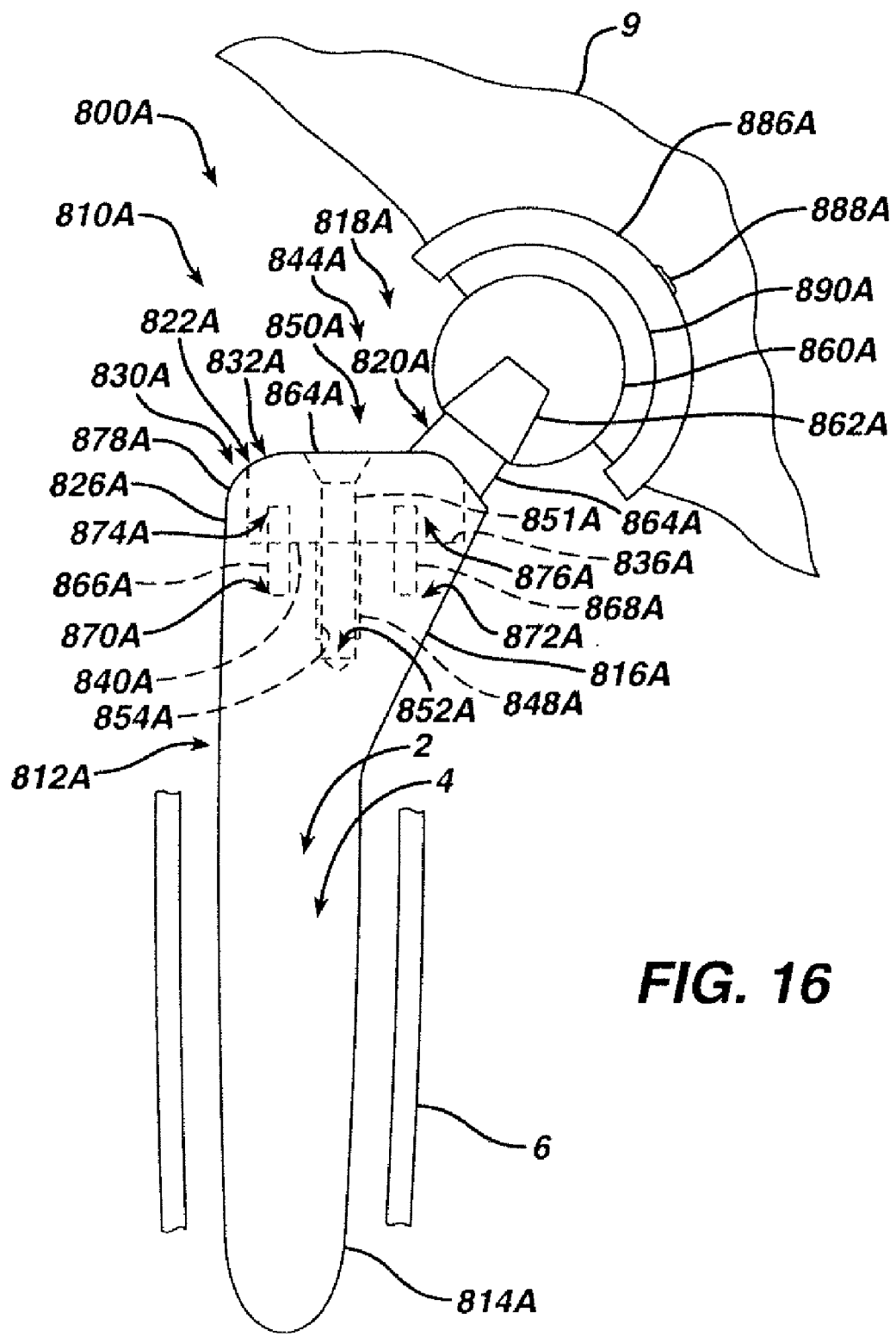
FIG. 16 is a plan view of the modular hip stem of FIGS. 14 and 15.

According to the present invention and referring now to FIGS. 14-16, yet another embodiment of the present invention is shown as prosthesis 800A. The prosthesis 800A is shown in FIG. 14 in the form of a hip prosthesis. The prosthesis 800A includes a hip stem 810A. The hip stem 810A is similar to the hip stem 810 of FIG. 13 except the hip stem 810A provides for posterior version for hip stems for both the right leg and the left leg of the patient. The hip stem 810A includes a stem component 812A as well as a right neck component 818A as shown in FIG. 14 and a left neck component 819A as shown in FIG. 15.

As shown in FIG. 16, the stem component 812A may be similar to the stem component 812 of FIG. 13. The stem component 812A includes a distal stem portion 814A adapted to fit within cavity 2 of the canal 4 of femur 6. The stem component 812A further includes a proximal body portion 816A extending from the distal stem portion 814A of the stem component 812A. The proximal body portion 816A includes an aperture 852A extending inwardly from inner face 836A of the proximal body portion 816A of the stem component 812A. Internal threads 854A are formed in the aperture 852A. The internal threads 854A cooperate with external threads 848A formed on screw 851A.

The right neck component 818A and the left neck component 819A are thus alternatively connected to the stem component 182A. The components 818A and 819A may be connected to the stem component 812A by any suitable connector.

The right neck component 818A is shown connected to the stem component 812A in FIG. 16. It should be appreciated that the left neck component 819A is likewise, similarly connected to the stem component 812A.

The right neck component 818A is, as is shown in FIG. 16, connected to the stem component 814A by, for example, connector 844A. The connector 844A, as is shown in FIG. 16 includes the screw 851A, as well as, a first pin 866A. The connector 844A may further include a second pin 868A spaced from and parallel to the first pin 866A.

The right neck component 818A includes a distal body portion 822A and a proximal neck portion 820A extending from the distal body portion 822A. The distal body portion 822A includes an aperture 850A for receiving the screw 851A. The distal body portion 822A further includes a first pin neck opening 874A for cooperating with the first pin 866A and a second pin neck opening 876A for cooperating with the second pin 868A. The distal body portion 822A further defines a planar face 840A for cooperation with an inner face 836A of the stem component 812A.

The proximal body portion 816A of the stem component 812A includes a first pin stem opening 870A for cooperation with the first pin 866A and a second pin stem opening 872A for cooperation with the second pin 868A. The proximal body portion 816A of the stem component 812A includes a sleeve portion 826A defining a pocket 832A for receiving periphery 878A of the distal body portion 822A of the right neck component 818A.

As shown in FIG. 14, the proximal neck portion 820A of the right neck component 818A includes a right neck 864A as well as a right external taper 862A extending from the right neck 864A. The right neck 864A extends posteriorly from the distal body portion 822A of the right neck component 818A at an angle θθ of, for example, 10 to 40 degrees. The posterior extension is intended to mimic the geometry of the natural right femur.

As shown in FIG. 15, the proximal neck portion 821A of the left neck component 819A includes a left neck 865A as well as a left external taper 863A extending from the left neck 865A. The left neck 865A extends posteriorly from the distal body portion 823A of the left neck component 819A at an angle θθθ of, for example, 10 to 40 degrees. While as shown in FIG. 15 the neck 865A extends downwardly, it should be appreciated that shape when placed in a left femur will extend posteriorly. The posterior extension is intended to mimic the geometry of the natural left femur.

It should be appreciated that both the right neck component 818A of FIG. 14 and the left neck component 819A of FIG. 15 may be used with the identical stem component 812A. This may be accomplished by providing the left external taper 863A of the left neck component 819A with identical dimensions to that of the right external taper 862A of the right neck component 818A. Thus both the right external taper 862A and the left external taper 863A may mate with the internal taper of the stem component 812A.

Referring again to FIG. 16, in addition to hip stem 810A, the prosthesis 800 further includes a head 860A, which matingly fits on external taper 862A or 863A of either of the neck components 818A and 819A respectively. The prosthesis 800A further includes an acetabular cup 886A for cooperation with acetabulum 9 of the patient. The acetabular cup 886A may include a feature in the form of, for example, a porous coated surface 888 for promoting boney in-growth between the acetabulum 9 and the acetabular cup 886A. The prosthesis 800A may include a bearing 890A positioned between the acetabular cup 886A and the head 860A. It should be appreciated that the acetabular cup 886A may directly cooperate with the head 860A.

It should be appreciated that the hip stem 810A, head 860A, acetabular cup 886A, and bearing 890A may be made of any suitable durable material. The hip stem 810A including the distal stem portion 814A, the neck components 818A and 819A, as well as the pins 866A and 868A and the screw 864A, may all be made of a suitable durable material. The materials for the components of the prosthesis 800A may, for example, be made of a plastic, a metal, or a composite. The material for which the prosthesis is made preferably is compatible with the human anatomy. The prosthesis 800A, if made of a metal may, for example, be made of a cobalt chromium alloy, a stainless steel alloy, or a titanium alloy.

The bearing 890A of the prosthesis 800A may for example, be made of a metal, a ceramic, or a plastic. The head 860A may be made of a metal, or a ceramic.

Figure 17:
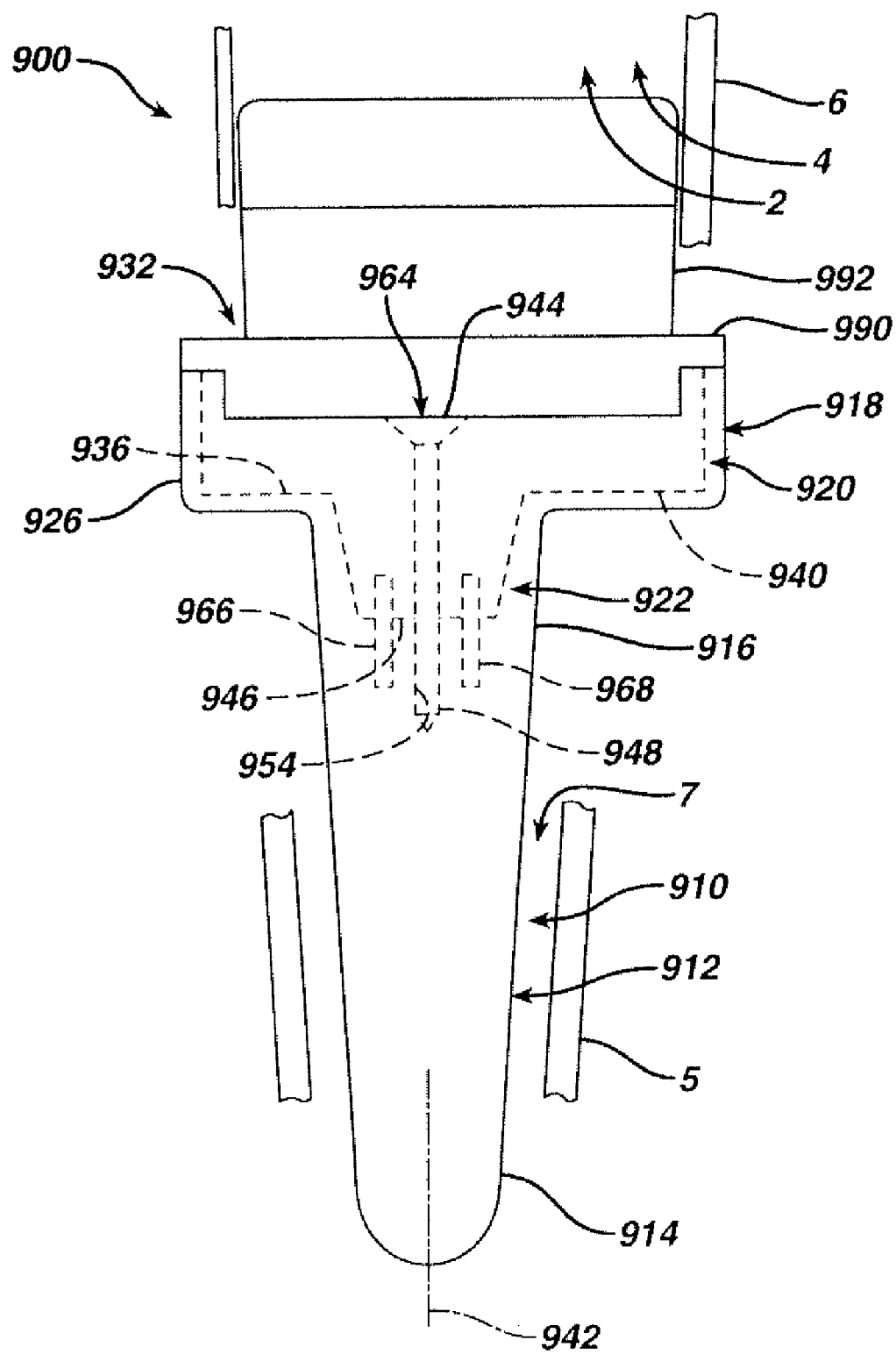
FIG. 17 is a plan view of a modular stem in accordance with a further embodiment of the present invention in the form of a tibial tray assembly implanted in the tibia.

According to the present invention and referring to FIG. 17 another embodiment of the present invention is shown as prosthesis 900. The prosthesis 900 as shown in FIG. 17 is for use in the knee joint. The orthopedic prosthesis 900 as shown in FIG. 16 includes a tibial component 910, a bearing 990 and a femoral component 992.

The tibial component 910 for the prosthesis 900 is for use with tibia 5. The tibial component 910 includes a joint component 918 and a stem component 912. The stem component 912 fits within the intramedullary canal 7 of the tibia 5. The stem component 912 includes a distal stem portion 914 as well as a proximal body portion 916. Proximal body portion 916 of the stem component 912 defines a pocket 932 formed from sleeve portion 926 of the proximal body portion 916. A connector 944 is used to connect the stem component 912 to the joint component 918.

The joint component 918 includes an articulation portion 920 and a distal body portion 922 extending from the articulation portion 920. The distal body portion 922 of the joint component 918 defines a protrusion 946 which cooperates with the pocket 932 formed by the sleeve 926 of the stem component 912.

The connector 944 connects the joint component 918 to the stem component 912. The connector 944 may have any suitable shape and may, as shown in FIG. 17, include a screw 964 as well as a first pin 966 and a second pin 968. The pins 966 and 968 engage with the joint component 918 and with the stem component 912. The screw 964 includes external threads 948 which cooperate with internal threads 954 formed on the proximal body portion 916 of the stem component 912. As shown in FIG. 17, the articulation portion 920 of the joint component 918 extends transversely or perpendicular to longitudinal axis 942 of the stem component 912 substantially past the stem component 912.

The sleeve 926 may extend, as shown in FIG. 17, up against the taper of the pocket 932. The sleeve 926 may, as shown in FIG. 17, extend out transversely from the longitudinal axis 942 and define a planer surface 936 of the stem component 912. Similarly, the joint component 918 may include a planer portion 940 extending transversely from the longitudinal axis 942. The planer portions 936 and 940 may cooperate with each other to support and form the stem component 912.

As shown in FIG. 17, the orthopedic prosthesis 900 further includes a femoral component 992 connected to cavity 2 formed in canal 4 of the femur 6. The femoral component 992 cooperates with the joint component 918 of the stem 912. The femoral component 992 may cooperate directly with the tibial component 910. The orthopedic prosthesis 900 may further include a bearing 990 supported by the articulating portion 920 of the joint component 918. The bearing 990 may, for example, be made of a pliable material, for example, a plastic.

The femoral component 992 and the stem component 912 may be made of any suitable material, for example, a plastic, a composite, or a metal and if made of a metal, for example, cobalt chromium alloy, stainless steel alloy, or titanium alloy.

Figure 18:
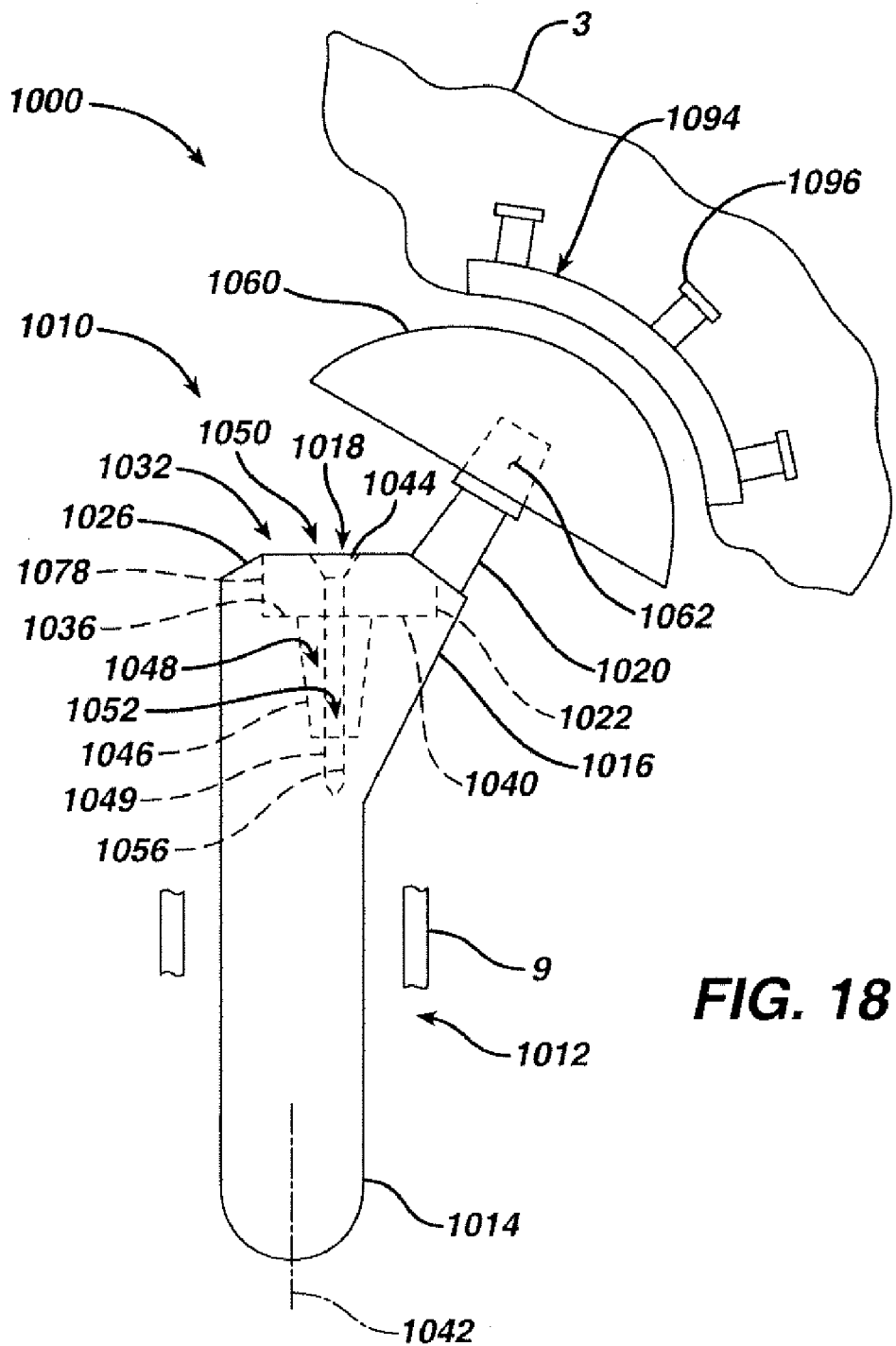
FIG. 18 is a plan view of a further embodiment of the modular stem of the present invention in the form of a modular shoulder prosthesis implanted in the humerus and glenoid cavity.

Referring now to FIG. 18, yet another embodiment of the present invention is shown as shoulder prosthesis 1000. The shoulder prosthesis 1000 includes a stem 1010 and a glenoid 1094. The stem 1010 includes a stem component 1012 for cooperation with humerus 9.

The stem component 1012 includes a distal stem portion 1014 and a proximal body portion 1016. The proximal body portion 1016 includes a sleeve 1026 defining a pocket 1032 therein. Within the pocket 1032 a stem planer face 1036 is formed. Extending distally from the stem planer face 1036 is a tapered aperture 1048. Extending distally from the tapered aperture 1048 is a cylindrical aperture 1052 having internal threads 1056 formed thereon.

The stem 1010 further includes a neck component 1018 having a distal body portion 1022 and a proximal neck portion 1020. The distal body portion 1022 defines an aperture 1050 therein.

The distal body portion 1022 defines a distal body planer face 1040 as well as a periphery 1078. The periphery 1078 and the neck planer face 1040 cooperate with pocket 1032 to position the neck component 1018 with the stem component 1012. The neck component 1018 further includes a protrusion 1046 extending from the planer face 1040. The protrusion 1046 matingly fits with the aperture 1048 to provide a taper-lock of the neck component 1018 to the stem component 1012.

While the neck component 1018 may be securely fastened to the stem component 1012 by means of the protrusion in taper lock, it should be appreciated that the shoulder prosthesis 1000 may further include a connector in the form of a screw 1044. The screw 1044 fits within the aperture 1050 of the neck component 1018 and includes external threads 1049 that cooperate with the internal threads 1056 formed on the stem component 1012.

The proximal neck portion 1020 includes an external taper 1062. The external taper 1062 is adapted to receive head 1060. The head 1060 cooperates with glenoid 1094 secured to glenoid facia 3 by pigs 1086. Stem 1010, head 1060, and glenoid 1094 may be made of any suitable durable material. The stem 1010 including the stem component 1012 and the neck component 1018 as well as the screw 1044 may be made, for example, of a plastic, a metal, or a composite. If made of a metal, the neck component 1018, stem component 1012, and screw 1044 may be made of, for example, a cobalt chromium alloy, a stainless steel alloy, or a titanium alloy. The glenoid 1094 may be made of a metal or be made of, for example, a more pliable material, for example, a plastic.

Figure 19:
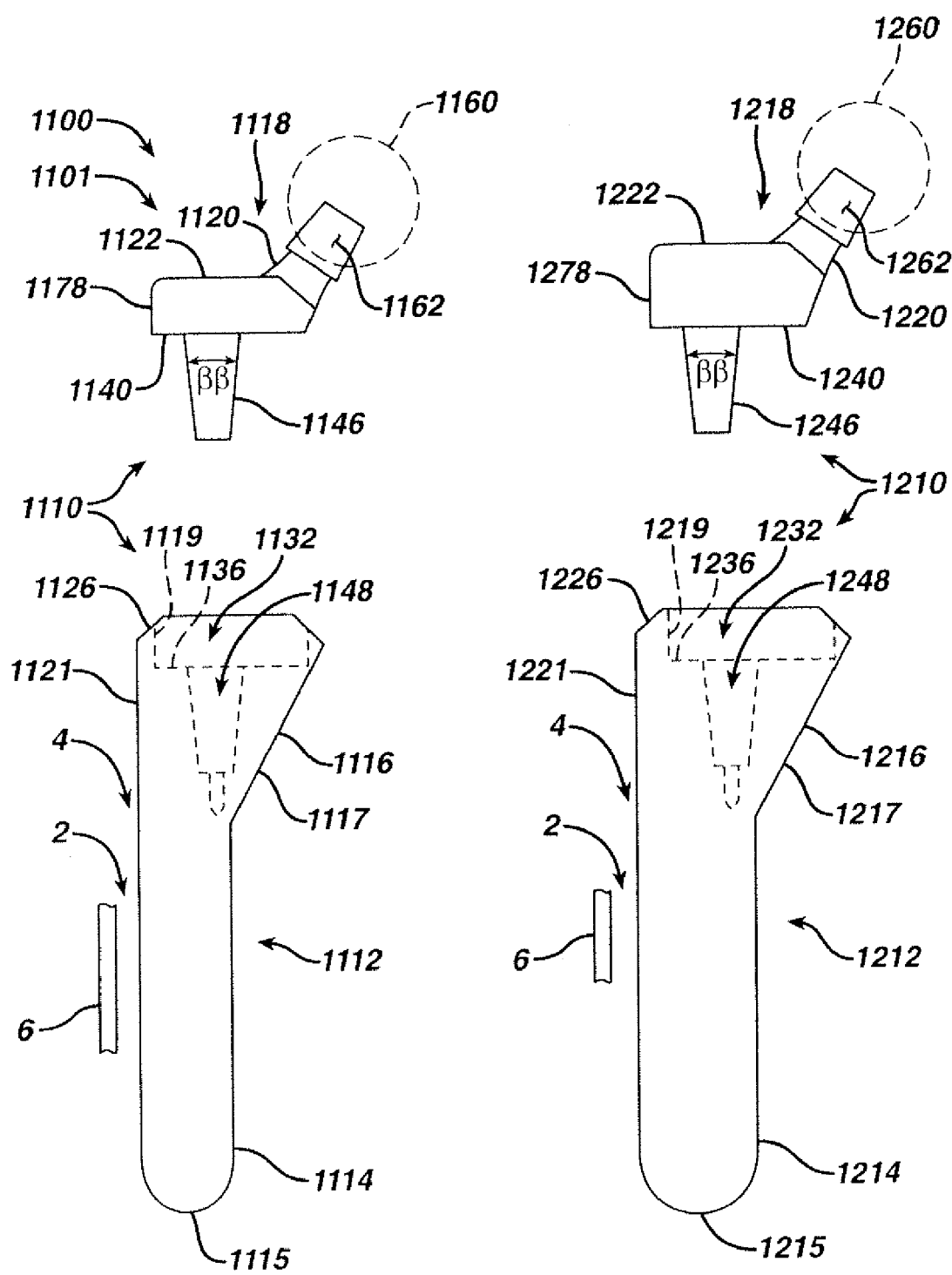
FIG. 19 is a plan view of a kit for performing joint arthoplasty including the modular stem of the present invention.

Referring now to FIG. 19, yet another embodiment of the present invention is shown as kit 1100. The kit 1100 includes the trial hip stem 1110 and the implant hip stem 1210. The trial hip stem 1110 and the implant hip stem 1210 preferably have similar, if not almost identical, shapes and dimensions. The trial 1110 is implanted into the body and used to perform a trial reduction or to verify the dimensions and selection of the hip stem components. The trial is removed after a trial reduction and the corresponding implant is permanently secured into the bone of the patient. The use of the trial verifies the selection of the implant and if the trial selection is believed to be sub-optimum, an alternate trial is used in the patient and if that alternate trial is found to be optimum, its corresponding implant is then implanted into the patient.

Trial 1110 includes a trial stem component 1112 and a trial neck component 1118. The trial stem component 1112 includes a distal stem portion 1114 and a proximal body portion 1116. The proximal body portion 1116 includes a sleeve portion 1126 defining a pocket 1132 and a surface 1136. Extending distally from the surface 1136 is a cavity 1148.

The trial 1110 further includes the trial neck component 1118. The trial neck component 1118 includes a distal body portion 1122 and a proximal neck portion 1120. The distal body portion 1122 includes a periphery 1178 for fitting against a sleeve portion 1126 of the stem component 1112. The distal body portion 1122 further includes a surface 1140 for mating with the surface 1136 of the stem component 1112. The distal body portion 1122 also includes a protrusion 1146 which mates with cavity 1148 of the stem component 1112. The protrusion 1146 defines included angle ββ.

The angle ββ is selected to provide for a self-locking taper between protrusion 1146 and the cavity 1148. The angle ββ may be, for example, from two to twenty degrees (2°-20°).

The angle ββ is preferably selected by the formula:

$$\tan \beta\beta/2 < \mu$$

where: β=coefficient of friction
ββ=included angle

The proximal neck portion 1120 includes an external taper 1162 to which head 1160 is matingly fitted.

The implant hip stem 1210 has a size and shape the same as trial 1110. For example, the implant 1210 includes a stem component 1212 having a distal stem 1212 portion 1214 and a proximal body portion 1216. The proximal body portion 1216 includes a sleeve portion 1226 defining pocket 1232. The pocket 1232 includes a surface 1236 as well as a cavity 1248 extending below the surface 1236.

The implant hip stem 1210 also includes a neck component 1218 including a distal body portion 1222 and a proximal neck portion 1220. The distal body portion 1222 defines a periphery 1278 thereof, as well as a surface 1240 of the distal body portion 1222. A protrusion 1246 extends downwardly from the surface 1240 and defines an included angle ββ. The proximal neck portion 1220 includes an external taper 1262 to which head 1260 is matingly fitted.

The trial stem component 1112 may be first implanted into the patient and the trial neck component 1118 may be secured to the trial stem component 1112. Alternatively, the implant stem component 1212 may be permanently secured to the patient and the trial neck component 1118 may be fitted to the implant stem component 1212.

The trial neck component 1118 may be secured to the implant stem component 1212 and a trial reduction made. If the trial reduction is satisfactory, the implant neck component 1218, which is identical to the trial neck component 1118, may be implanted into the patient. If, however, the trial neck component 1118 is found in a trial reduction to not be optimum, an alternate trial neck component may be utilized in a trial reduction attempted with the new trial neck component. If that second trial neck component is found to be satisfactory, a corresponding implant neck component is then implanted.

According to the present invention and referring again to FIG. 19, a kit 1101 for use in performing joint arthroplasty is shown. The kit 1101 includes the orthopaedic stem trial or trial hip stem 1110 for use in performing joint arthroplasty. The trial 1110 may be fitted to a cavity 2 in the canal 4 of a long bone 6 and assists in performing a trial reduction in performing joint arthroplasty. The orthopaedic stem trial 1110 includes canal component or trial stem component 1112 having an external periphery 1113. A portion of the canal component 1112 may be fitted to the cavity 2 in the canal 4 of the long bone 6. The canal component 1112 includes distal stem portion or canal portion 1114 that has a first end 1115 for insertion into the cavity 2 and an opposed second end 1117. The canal component 1112 further includes a sleeve portion 1126 extending from the second end 1117 of the canal portion 1114. The sleeve portion 1126 has an internal periphery 1119 that defines pocket or internal cavity 1132. The sleeve portion 1126 also has an external periphery 1121.

The orthopaedic stem trial 1112 also includes trial neck component or joint component 1118 removably connectable to the canal component 1112. The joint component 1118 has neck portion or body portion 1120 and distal body portion or connection portion 1122. The connection portion 1122 of the joint component 1118 defines an external periphery 1178. A portion of the external periphery 1121 of the sleeve portion 1126 may be fitted to the cavity 2 of the long bone 6. At least a portion of the external periphery 1178 of the connection portion 1122 of the joint component 1118 may be fitted into the internal cavity 1132 of the sleeve portion 1126 so that the external periphery 1178 of the connection portion 1122 of the joint component 1118 is spaced inwardly from the external periphery 1121 of the sleeve portion 1126 of the stem component 1112 when the joint component 1118 is fixedly connected to the stem component 1112 so that the joint component 1118 may be removed from the long bone 6.

The kit 1101 includes orthopaedic hip stem or orthopaedic stem implant 1210 for use in performing joint arthroplasty. The implant 1210 may be fitted to cavity 2 in canal 4 of long bone 6 to perform a joint arthroplasty. The orthopaedic stem implant 1210 includes implant stem component or canal component 1212 having an external periphery 1221. At least a portion of the canal component 1212 may be fitted to the cavity 2 in the canal 4 of the long bone 6. The canal component 1212 includes distal stem portion or canal portion 1214 having a first end 1215 for insertion into the cavity 2 and an opposed second end 1217. The canal component 1212 further includes sleeve portion 1226 extending from the second end 1217 of the canal portion 1214. The sleeve portion 1226 has an internal periphery 1219 that defines pocket or internal cavity 1232. The sleeve portion 1226 also has an external periphery 1221. The orthopaedic stem implant 1210 also includes implant neck component or joint component 1218 that may be removably connected to the canal component 1212. The joint component 1218 has distal body portion or connection portion 1222 and neck portion or body portion 1220. The connection portion 1222 of the joint component 1218 defines external periphery 1278. A portion of external periphery 1221 of the sleeve portion 1226 may be fitted to the cavity 2 of the long bone 6. A portion of the external periphery 1278 of the connection portion 1222 of the joint component 1218 may be fitted into the internal cavity 1232 of the sleeve portion 1226. The external periphery 1278 of the connection portion 1222 of the joint component 1218 is spaced thereby inwardly from the external periphery 1221 of the sleeve portion 1226 of the stem component 1212. This is accomplished when the joint component 1218 is fixedly connected to the stem component 121. The joint component 1218 may thereby be removed from the long bone without disturbing the fixation of the stem component 1212 to the long bone 6.

Figure 20:
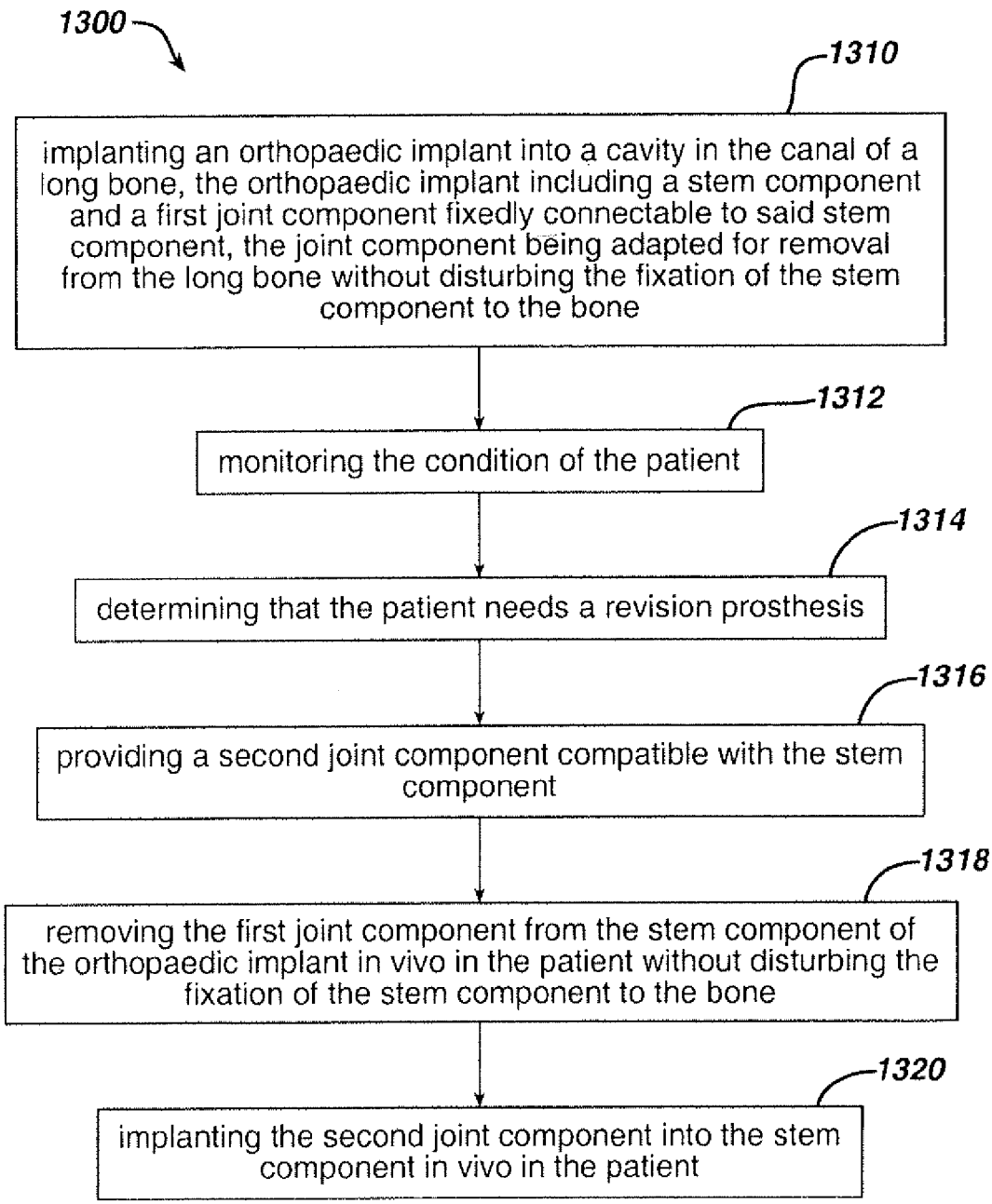
FIG. 20 is a process flow diagram of a method of performing joint arthroplasty surgery in accordance with yet another embodiment of the present invention.

Referring now to FIG. 20, yet another embodiment of the present invention is shown as method 1300 for treating orthopedic joint disease of the patient. The method 1300 includes a first step 1310 of implanting an orthopedic implant into a cavity in the canal of the long bone. The orthopedic implant includes a stem component and a first joint component fixedly connectable to the joint component. The joint component is adapted for removal from the long bone without disturbing the fixation of the stem component to the bone. The method 1300 includes a second step 1312 of monitoring the condition of the patient and a third step 1314 of determining that the patient needs a revision prosthesis. The method 1300 also includes a fourth step 1316 of providing a second joint component compatible with the stem component. The method 1300 further includes a fifth step 1318 of removing the first joint component from the stem component of the orthopedic implant in vivo without disturbing the fixation of the stem component to the bone the orthopedic implant. The method 1300 further includes a sixth step 1320 of implanting the second joint component into the stem component in vivo in the patient.

Figure 21:
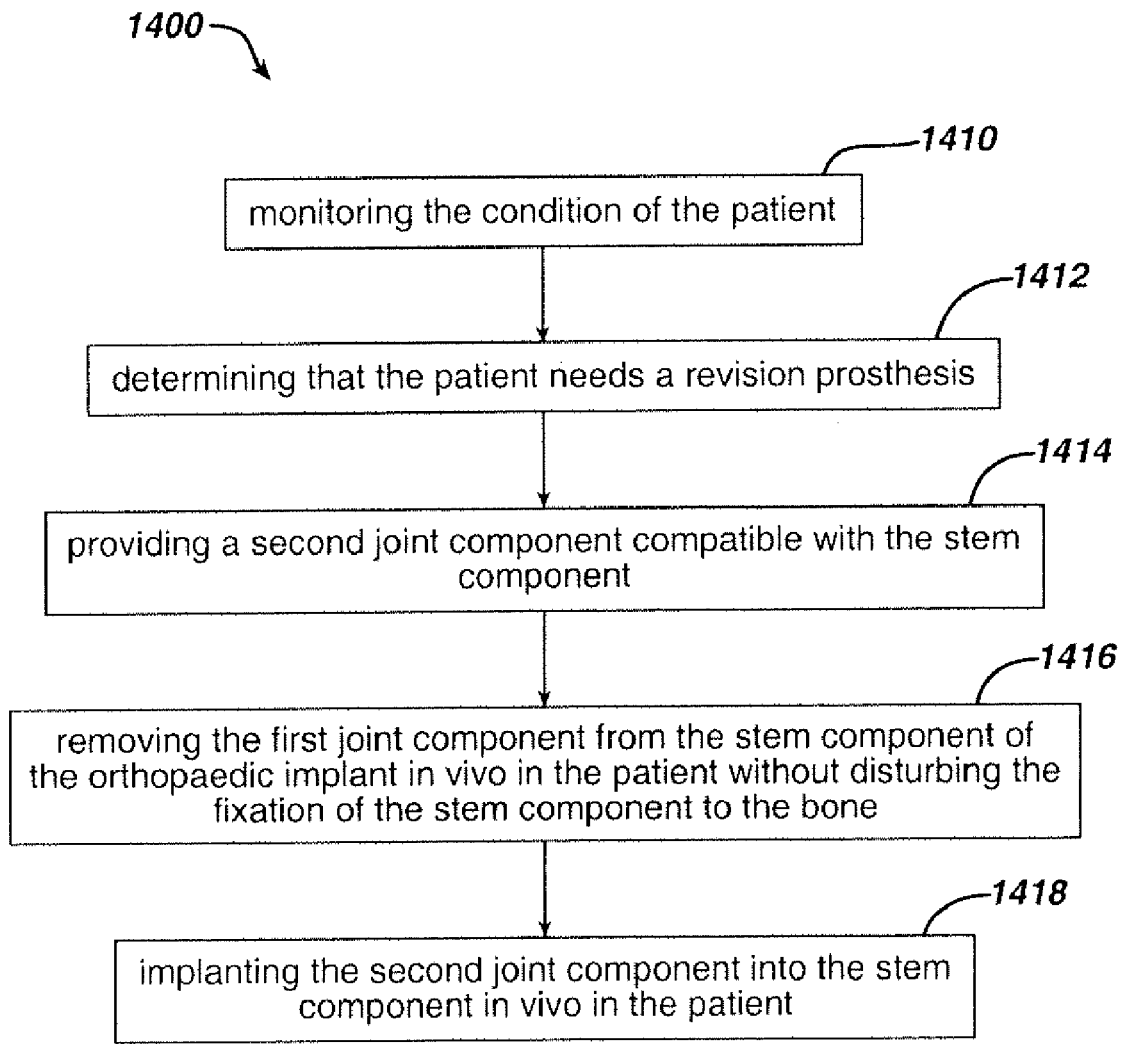
FIG. 21 is a process flow diagram for a method of performing joint arthroplasty surgery according to a further embodiment of the present invention.

According to the present invention and referring now to FIG. 21, yet another embodiment of the present invention is shown as surgical method 1400. The method 1400 represents a method for providing revision joint arthroplasty on a patient having an orthopedic implant. The orthopedic implant includes a stem component and a first joint component fixedly connectable to the stem component. The joint component is adapted for removal from the long bone without disturbing the fixation of the stem component to the bone. The method 1400 includes a first step 1410 of monitoring the condition of the patient and a second step 1412 of determining whether the patient needs a revision prosthesis. The method 1400 includes a third step 1414 of providing a second joint component compatible with the stem component. The method 1400 further includes a fourth step 1416 of removing the first joint component from the stem component of the orthopedic implant in vivo in the patient without disturbing the fixation of the stem component to the bone. The method 1400 further includes a fifth step 1418 of implanting the second joint component in vivo in the patient.

Figure 22:
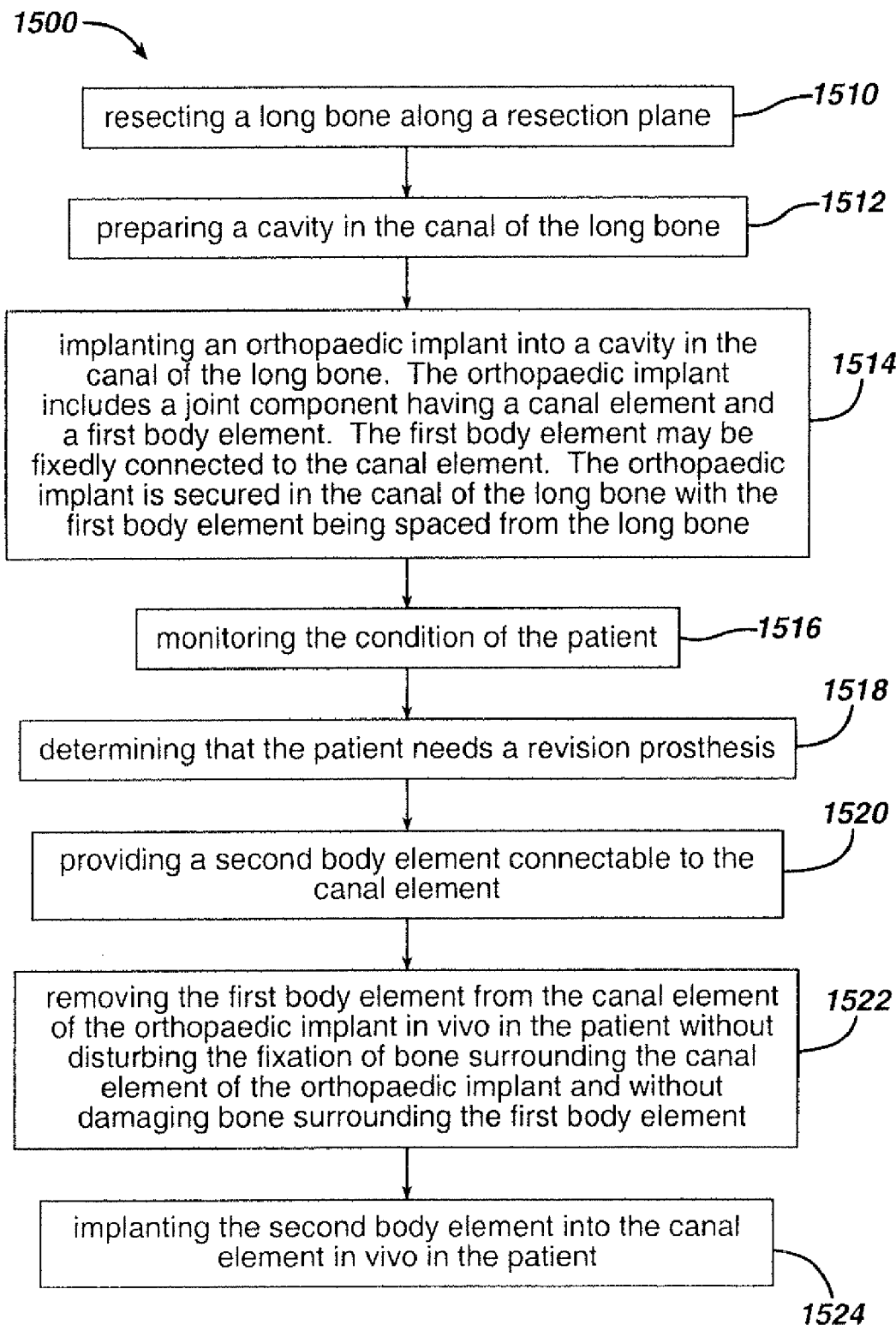
FIG. 22 is a process flow diagram of a method of performing joint arthroplasty surgery in accordance with yet another embodiment of the present invention.

Referring now to FIG. 22, another aspect of the present invention is shown as method 1500 for treating orthopaedic joint disease of a patient. The method 1500 includes a first step 1510 of resecting a long bone along a resection plane and a second step 1512 preparing a cavity in the canal of the long bone. The method also includes a third step 1514 of implanting an orthopaedic implant into a cavity in the canal of the long bone. The orthopaedic implant includes a joint component having a canal element and a first body element. The first body element may be fixedly connected to the canal element. The orthopaedic implant is secured in the canal of the long bone with the first body element being spaced from the long bone. The method further includes a fourth step 1516 of monitoring the condition of the patient and a fifth step 1518 of determining that the patient needs a revision prosthesis. The method also includes a sixth step 1520 of providing a second body element connectable to the canal element and a seventh step 1522 of removing the first body element from the canal element of the orthopaedic implant in vivo in the patient without disturbing the fixation of bone surrounding the canal element of the orthopaedic implant and without damaging bone surrounding the first body element. The method further includes an eighth step 1524 of implanting the second body element into the canal element in vivo in the patient.

Figure 23:
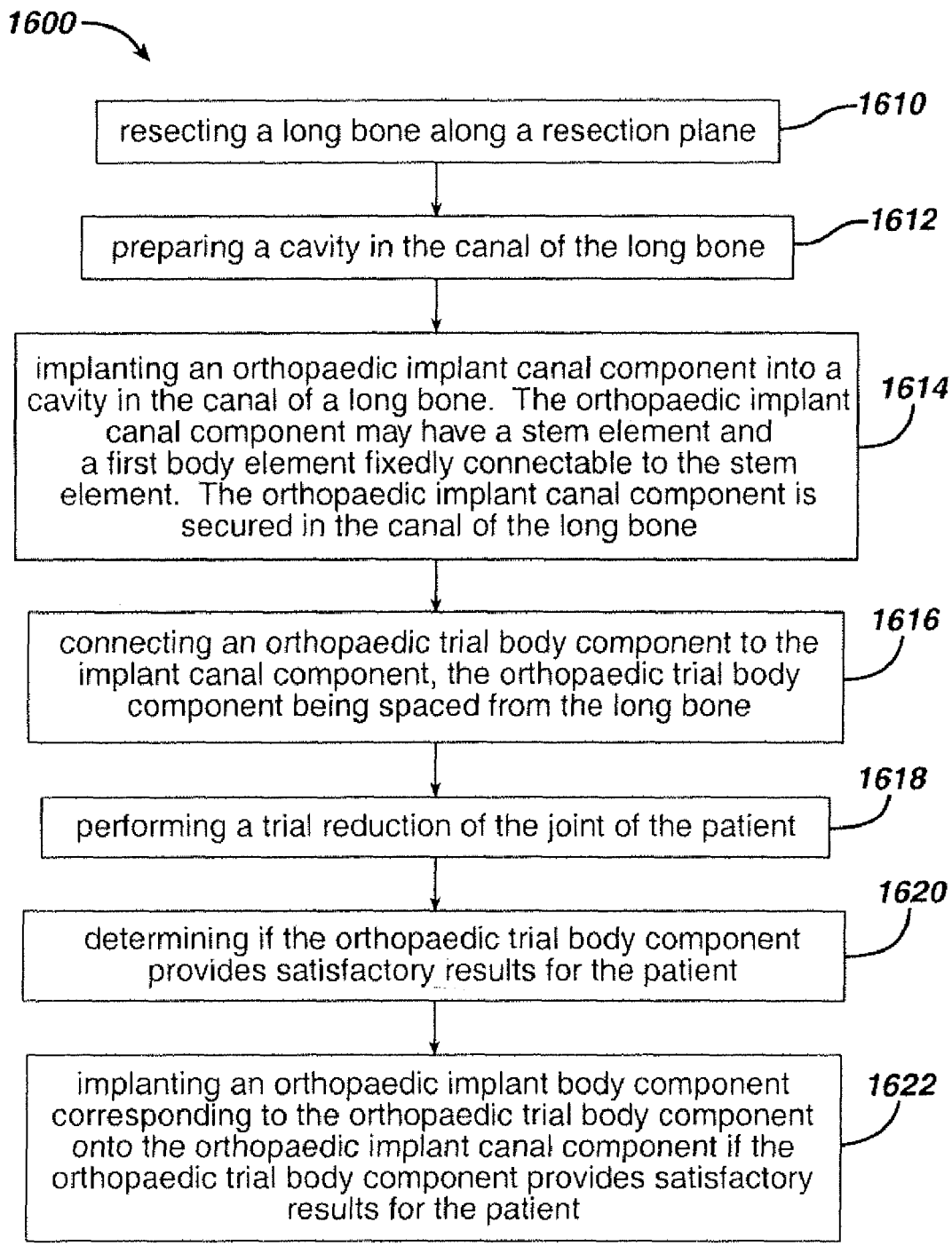
FIG. 23 is a process flow diagram for a method of performing joint arthroplasty surgery according to a further embodiment of the present invention.

Referring now to FIG. 23 a method 1600 for providing joint arthroplasty on a joint of a patient with an orthopaedic implant is shown. The method 1600 includes a first step 1610 of resecting a long bone along a resection plane and a second step 1612 of preparing a cavity in the canal of the long bone. The method also includes a third step 1614 of implanting an orthopaedic implant canal component into a cavity in the canal of a long bone. The orthopaedic implant canal component may have a stem element and a first body element fixedly connectable to the stem element. The orthopaedic implant canal component is secured in the canal of the long bone. The method further includes a fourth step 1616 of connecting an orthopaedic trial body component to the implant canal component, the orthopaedic trial body component being spaced from the long bone and a fifth step 1618 of performing a trial reduction of the joint of the patient. The method also includes a sixth step 1620 of determining if the orthopaedic trial body component provides satisfactory results for the patient and a seventh step 1622 of implanting an orthopaedic implant body component corresponding to the orthopaedic trial body component onto the orthopaedic implant canal component if the orthopaedic trial body component provides satisfactory results for the patient.

The third step 1614 of implanting the canal component step may further include permanently securing the canal component to the long bone.

The third step 1614 of implanting the canal component step may further include positioning the canal component such that the canal component intersects the resection plane.

Figure 24:
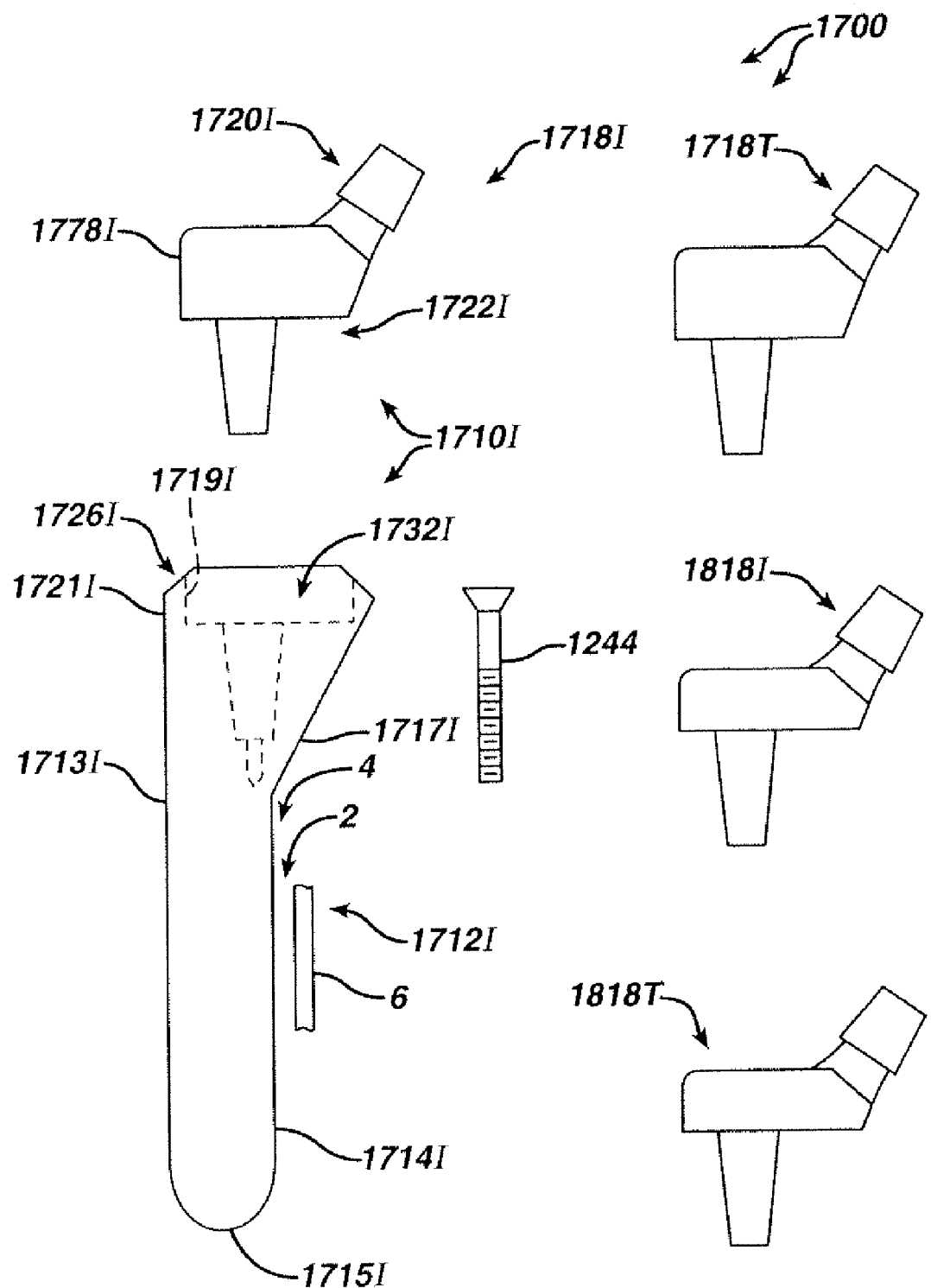
FIG. 24 is a plan view of another kit for performing joint arthroplasty including the modular stem of the present invention.

Referring now to FIG. 24 the present invention may be in the form of a kit 1700 for use in performing joint arthroplasty. The kit 1700 includes a canal component implant 1712I having an external periphery 1713I. A portion of the canal component implant 1712I may be fitted to a cavity 2 in a canal 4 of a long bone 6. The canal component implant 1712I includes a canal portion 1714I. The canal portion 1714I has a first end 1715I for insertion into the cavity 2 and an opposed second end 1717I.

The canal component implant 1712I further including a sleeve portion 1726I extending from the second end 1717I of the canal portion 1714I. The sleeve portion 1726I has an internal periphery 1719I defining an internal cavity 1732I. The sleeve portion 1726I also has an external periphery 1721I. The kit 1700 also includes a first joint component implant removeably connectable to the canal component implant. The first joint component implant 1718I has a body portion 1720I and a connection portion 1722I. The connection portion 1722I of the first joint component implant 1718I has an external periphery 1778I. A portion of the external periphery 1778I of the connection portion 1722I of the first joint component implant 1718I may be fitted into the internal cavity 1732I of the sleeve portion 1726I of the canal component implant 1712I, so that the external periphery 1778I of the connection portion 1722I of the first joint component implant 1718I is spaced inwardly from the external periphery 1721I of the sleeve portion 1726I of the canal component implant 1712I when the first joint component implant 1718I is fixedly connected to the canal component implant 1712I so that the first joint component implant 1718I may be removed from the long bone 6 without disturbing the fixation of the canal component implant 1712I to the long bone 6.

The kit 1700 also includes a first joint component trial 1718T generally corresponding in size and shape with the first joint component implant 1718I. The first joint component trial 1718T may be removeably connected to the canal component implant 1712I. The first joint component trial 1718T having a body portion 1720T and a connection portion 1722T. The connection portion 1722T of the first joint component trial 1718T has an external periphery 1778T. A portion of the external periphery 1778T of the connection portion 1722T of the first joint component trial 1718T may be fitted into the internal cavity 1732I of the sleeve portion 1726I of the canal component implant 1712I. The external periphery 1778T of the connection portion 1722T of the first joint component trial 1718T is thereby spaced inwardly from the external periphery 1721T of the sleeve portion 1726T of the canal component implant 1712I. This occurs when the first joint component trial 1718T is fixedly connected to the canal component implant 1712I. The first joint component trial 1718T may thus be removed from the long bone 6 without disturbing the fixation of the canal component implant 1712I to the long bone 6.

The kit further includes a second joint component implant 1818I removeably connectable to the canal component implant 1712I. The second joint component implant 1818I has a body portion 1820I and a connection portion 1822I. The connection portion 1822I of the second joint component implant 1818I has an external periphery 1878I. A portion of the external periphery 1878I of the connection portion 1822I of the second joint component implant 1818I may be fitted into the internal cavity 1732I of the sleeve portion 1726I of the canal component implant 1712I so that the external periphery 1878I of the connection portion 1822I of the second joint component implant 1818I is spaced inwardly from the external periphery 1721I of the sleeve portion 1726I of the canal component implant 1712I when the second joint component implant 1818I is fixedly connected to the canal component implant 1712I so that the second joint component implant 1818I may be removed from the long bone 6 without disturbing the fixation of the canal component implant 1712I to the long bone 6.

The kit 1700 also includes a second joint component trial 1818T generally corresponding in size and shape with the second joint component implant 1818I. The second joint component trial 1818T may be removeably connectable to the canal component implant 1712I. The second joint component trial 1818T having a body portion 1820T and a connection portion 1822T. The connection portion 1822T of the second joint component trial 1818T has an external periphery 1878T. A portion of the external periphery 1878T of the connection portion 1822T of the second joint component trial 1818T may be fitted into the internal cavity 1732I of the sleeve portion 1726I of the canal component implant 1712I so that the external periphery 1878T of the connection portion 1822T of the second joint component trial 1818T is spaced inwardly from the external periphery 1721I of the sleeve portion 1726I of the canal component implant 1712I when the second joint component trial 1818T is fixedly connected to the canal component implant 1712I so that the second joint component trial 1818T may be removed from the long bone 6 without disturbing the fixation of the canal component implant 1712I to the long bone 6.

The kit 1700 permits the canal component implant 1712I to be permanently implanted. The kit 1700 also permits the first joint component trial 1718T to be assembled to the canal component implant 1712I and used to perform a trial reduction. The kit 1700 further permits the first joint component trial 1718T to be replaced with the second joint component trial 1818T if the trial reduction has unsatisfactory results.

Figure 25:
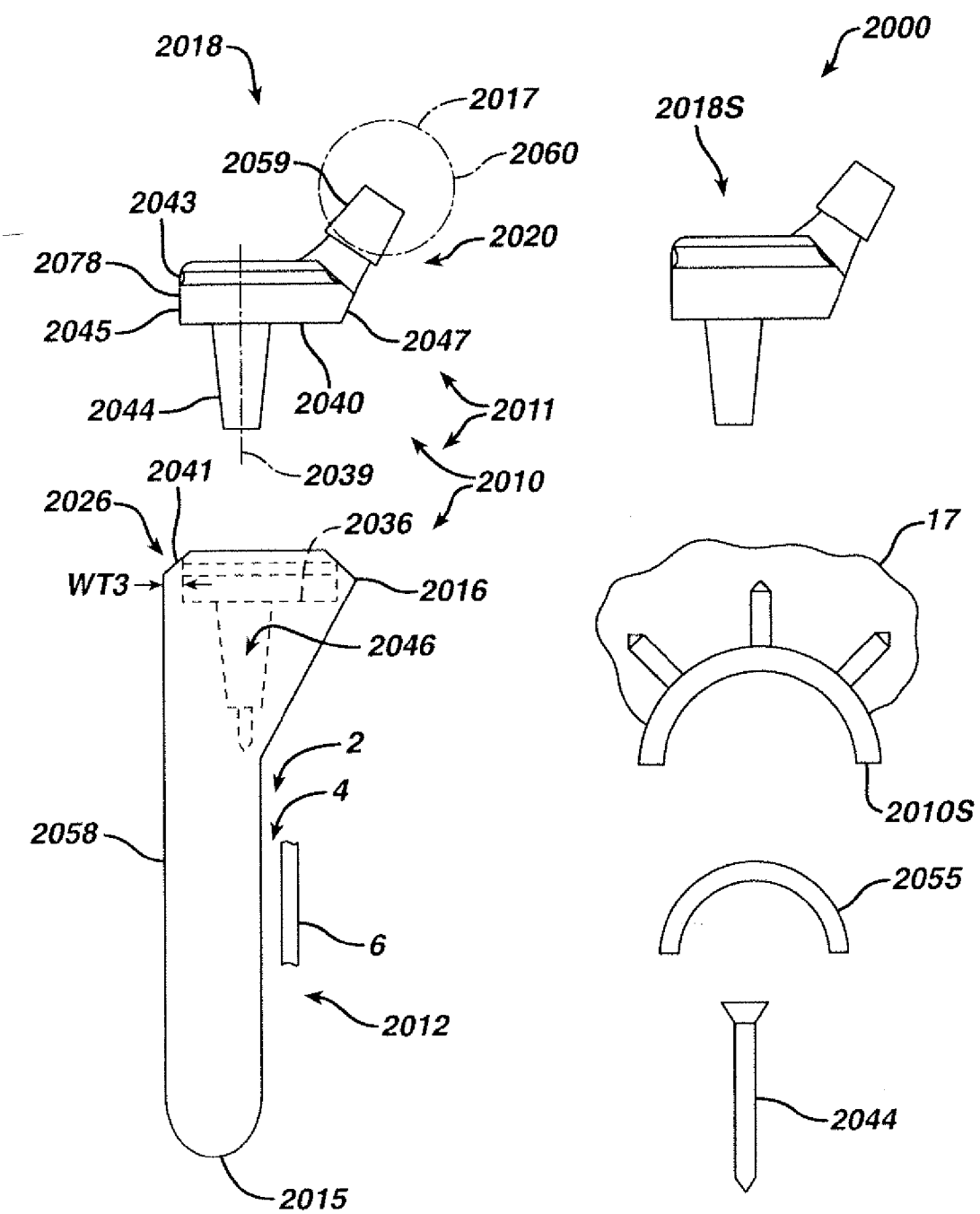
FIG. 25 is a plan view of a modular hip stem in accordance with a further embodiment of the present invention utilizing a location ring.

Referring now to FIG. 25, an orthopaedic implant 2011 is used to perform joint arthroplasty. A portion of the orthopaedic implant 2011 is capable of being fitted to cavity 2 in the canal 4 of long bone 6. The cavity 2 extends from a resected plane 11 of the long bone 6. The orthopaedic implant 2011 includes joint component 2010. The joint component 2010 includes stem element 2012 defining external periphery 2058 of the stem element 2012. The stem element 2012 has a first end 2015 for insertion into the cavity 2. The external periphery 2058 of the stem element 2012 has a stem resection ring 2041. The stem resection ring 2041 may be aligned with the resected plane 11 of the long bone 6.

The joint component 2010 also includes a first body element 2018 capable of being fixedly fitted to the stem element 2012. The first body element 2018 includes an external periphery 2078. The external periphery 2078 of the first body element 2018 has a body component ring 2043. The body component ring 2043 may be aligned with the resected plane 11 of the long bone 6. A canal portion 2045 of the first body element 2018 extends generally from the component ring 2043 of the external periphery 2078 of the first body element 2018 toward the first end 2015 of the stem element 2012 when the first body element 2018 is fixedly connected to the stem element 2012.

The external periphery 2047 of the canal portion 2045 of the first body element 2018 is spaced inwardly from external periphery 2058 of the stem element 2012 when the first body element 2018 is fixedly connected to the stem element 2012 so that the first body element 2018 may be removed from the long bone 6 without disturbing the fixation of the stem element 2012 to the long bone 6.

As shown in FIG. 25 the orthopaedic implant 2011 may be configured such that the first mentioned body element 2018 may be removably fixedly connected to the stem element 2012 and may include a second body element 2018S that may be removably fixedly connected to the stem element 2012. The first body element 2018 and the second body element 2018S may thus be interchangeably connected to the stem element 2012 while the stem element 2012 is implanted in the cavity 2 of the long bone 6.

The orthopaedic implant 2011 may have a portion of the stem element 2012 that extends over a portion of the first body element 2018.

The stem element 2012 of the orthopaedic implant, as shown in FIG. 25, may include a sleeve portion 2016. The sleeve portion 2016 may receive at least a portion of the canal portion 2045 of the first body element 2018.

The first body element 2018 of the orthopaedic implant 2011, as shown in FIG. 25, may be removably securable to the stem element 2012.

As shown in FIG. 25, a portion 2036 of the external periphery 2058 of the stem element 2012 may be generally planar. Also a portion 2040 of the external periphery of the body element 2018 may be generally planar. The portion 2036 of the external periphery 2058 of the stem element 2012 and the portion 2040 of the external periphery 2078 of the body element 2018 may be in contact with each other.

A connector 2044 may be used to connect the body element 2018 to the stem element 2012. The connector 2044 may be in the form of a screw or a pin (see FIG. 16).

The body element 2018 may include a protrusion 2044 extending from a surface of the connection element 2022. The stem element 2012 may include an aperture 2048 for receiving the protrusion 2046. It should be appreciated that the body may include an aperture (not shown) and the stem element may include a protrusion (not shown). The protrusion may be tapered.

The implant 2011 may further include second joint component 2010S for cooperation with a first joint component 2010. A portion of the external periphery of the body element 2018 may include an articulation surface 2017 for articulation with the second joint component 2010S.

The second joint component 2010S may be adapted for fixed implantation onto a second bone 17. A bearing component 2055 may be positioned between the first joint component 2010 and the second joint component 2010S. The bearing component 2055 articulates at the first joint component 2010 and is fixedly attached to the second joint component 2010S. Alternately the bearing component 2055 may articulate with the second joint component 2010S and be fixedly attached to the first joint component 2010.

As shown in FIG. 25, the orthopaedic implant 2011 may be in the form of a hip implant. The joint component 2010 is in the form of a hip stem. The orthopaedic implant 2011 may also include the second joint component 2010S in the form of an acetabular cup for articulating cooperation with the hip stem.

As shown in FIG. 25, the body element 2018 may include a tapered protrusion 2059. The orthopaedic implant 2011 may also include a generally spherical head 2060. The head 2060 may, as shown, be removably fixedly secured to the tapered protrusion 2059.

As shown in FIG. 1, the joint component defines a longitudinal axis 2039. The stem element 2012 may have a sleeve portion 2026. The sleeve portion 2026 may define a wall thickness WT3 of the sleeve portion 2026. The wall thickness WT3 may generally be uniform about the outer periphery 2058 of the stem element 2012 in a plane normal to the longitudinal axis 2039 of the joint component 2010 and may be defined by wall thickness WT3. The external periphery 2078 of the body element 2018 may, as shown, closely conform to the sleeve portion 2026 of the stem element 2012.

It should be appreciated that the orthopaedic implant 2011 may be in the form of a knee prosthesis, a hip prosthesis or a shoulder prosthesis.

Referring again to FIG. 25, it should be appreciated that the stem element 2012 may be interchangeably connectable to the first joint element 2018 and with the second joint element 2018S. The first joint element 2018 and the second joint element 2018S may as shown include a different dimension, or several different dimensions from each other. Thus, it should be appreciated that the stem element can receive joint elements of varying heights, offsets and degrees of version.

Continuing to refer to FIG. 25, the stem resection ring 2041 may be in the form of a recess. The recess 2041 may be a score mark or a machined or formed groove. It should be appreciated that the ring may likewise be a raised area or protrusion (not shown). It should be further appreciated that the ring 2041 may be acid etched or marked with ink or paint. It should be appreciated that the ring 2041 may be continuous or discontinuous around the stem 2012.

It should be appreciated that body element 2018 may likewise include body component ring 2043. The body component ring 2043 may have the same configuration as that of the stem resection ring 2041 and may be recessed or protruding.

It should be appreciated that the stem resection ring 2041 and/or the body component ring 2043 may, as shown in FIG. 25, be visually distinguishable from the external periphery 2058 of the stem element 2012 and/or the external periphery 2078 of the body element 2018.

It should likewise be appreciated that the stem resection ring 2041 and/or the body component ring 2043 may be visually indistinguishable from the external periphery 2058 of the stem element 2012 and/or the external periphery 2078 of the body element 2018. The stem resection ring 2041 and/or the body component ring 2043 may thus be invisible.

Figure 26:
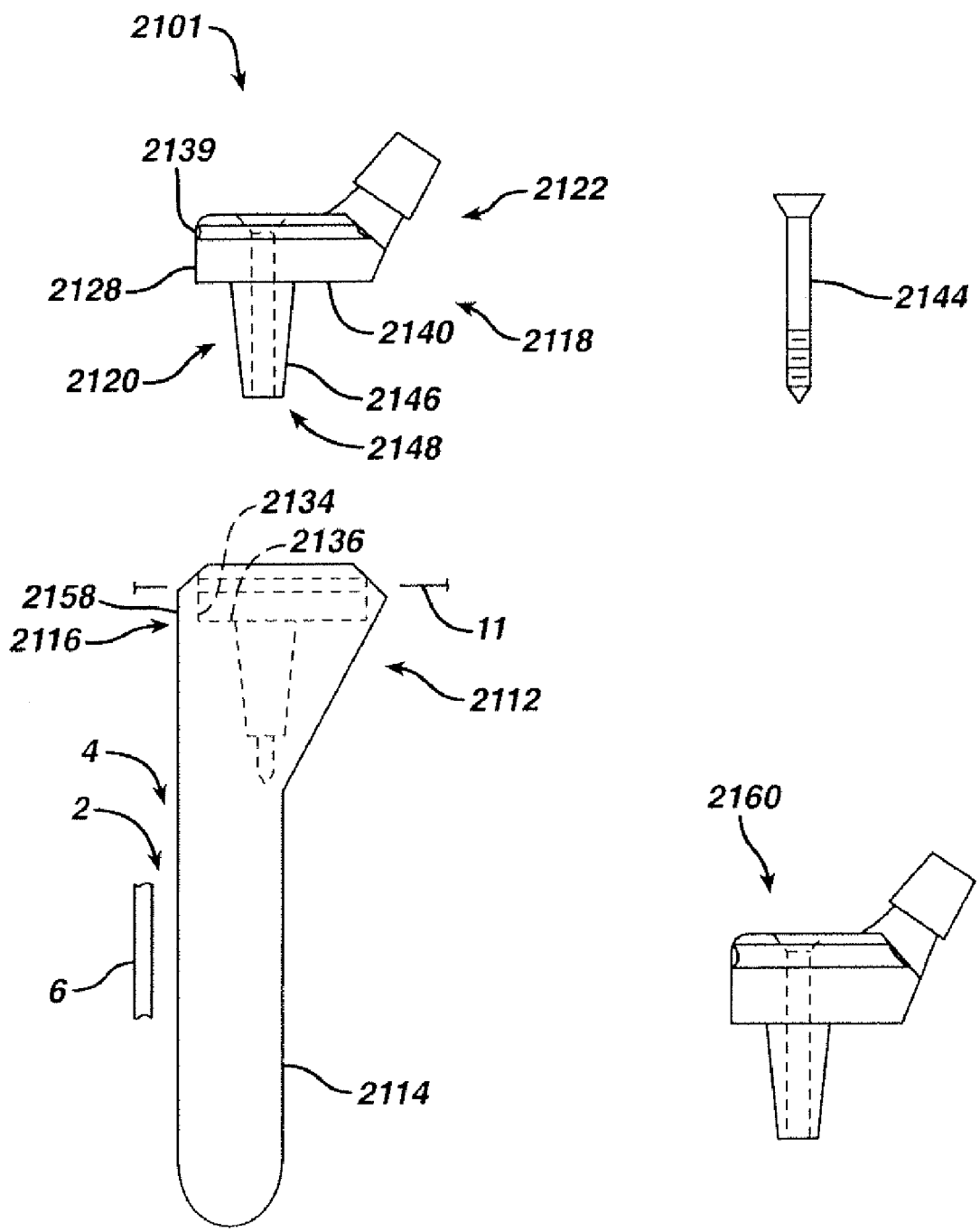
FIG. 26 is a plan view of a body component of a modular hip stem in accordance with a further embodiment of the present invention utilizing a location ring.

According to the present invention and referring to FIG. 26, a first joint component 2118 for use with a stem component 2112 having a canal portion 2114 and a sleeve portion 2116 for use as part of a prothesis 2101 in performing joint arthroplasty is shown. The sleeve portion 2116 of the stem component 2112 has an internal periphery 2134 and an external periphery 2158. A portion of the external periphery 2158 of the sleeve portion 2116 of the stem component 2112 may be fitted to a cavity 2 in the canal 4 of a long bone 6. The cavity 2 extends from a resected plane 11 of the long bone 6.

The first joint component 2118 includes a body portion 2122 and a connection portion 2120. The connection portion 2120 extends from the body portion 2122 and has an external periphery 2128. The external periphery 2128 of the connection portion 2120 may be positioned within the internal periphery 2134 of the sleeve portion 2116 of the stem component 2112.

The external periphery 2128 of the connection portion 2120 may include a connection resection ring 2139. The connection resection ring 2139 may be used for alignment with the resected plane 11 of the long bone 6. The external periphery 2128 of the connection portion 2120 is spaced inwardly from the external periphery 2158 of the sleeve portion 2116 of the stem component 2112 when the first joint component 2118 is fixedly connected to the stem component 2112 so that the joint component 2018 may be removed from the long bone 6 without disturbing the fixation of the stem component 2112 to the long bone 6.

As shown in FIG. 26, the connection portion 2120 of the first joint component 2118 may be adapted to be removably fixedly connected to the stem component 2112. Further the prosthesis 2101 may include a second joint component 2160 removably fixedly connectable to the stem component. The first joint component 2118 and the second joint component 2160 may, as shown, be interchangeably connected to the stem component 2112 while the stem component 2112 is implanted in the cavity 2 of the long bone 6.

As shown in FIG. 26, the connection portion 2120 of the first joint component 2118 may be adapted to fit within the internal periphery 2134 of the stem component 2112.

As shown in FIG. 26, a portion 2136 of the external periphery 2158 of the stem component 2112 may be generally planar. Further a portion 2140 of the external periphery 2128 of the first joint component 2118 may be generally planar. The portion 2136 of the external periphery 2158 of the stem component 2112 and the portion 2140 of the external periphery 2128 of the first joint component 2118 may, as shown, be adapted for contact with each other.

The first joint component 2118, as shown in FIG. 26, may include a feature 2148 for cooperation with a connector 2144 to connect the first joint component 2118 to the stem component 2112. The feature 2148 may be in the form of an aperture 2148 for passing the connector 2144 through the first joint component 2118. For example, the aperture 2148 may be a cylindrical aperture.

The first joint component 2118 as shown in FIG. 26 may include a protrusion 2146. Alternatively, the joint component may include an aperture (not shown). The protrusion 2146 may, as shown, be tapered.

It should be appreciated that first joint component 2118 may be in the form of a hip stem neck 2118.

The first joint component 2118 and the second joint component 2160 may, as shown in FIG. 26, be interchangeably connectable to the stem component 2112. Thereby the stem component 2112 can receive joint components of varying heights, offsets and degrees of version.

Figure 27:
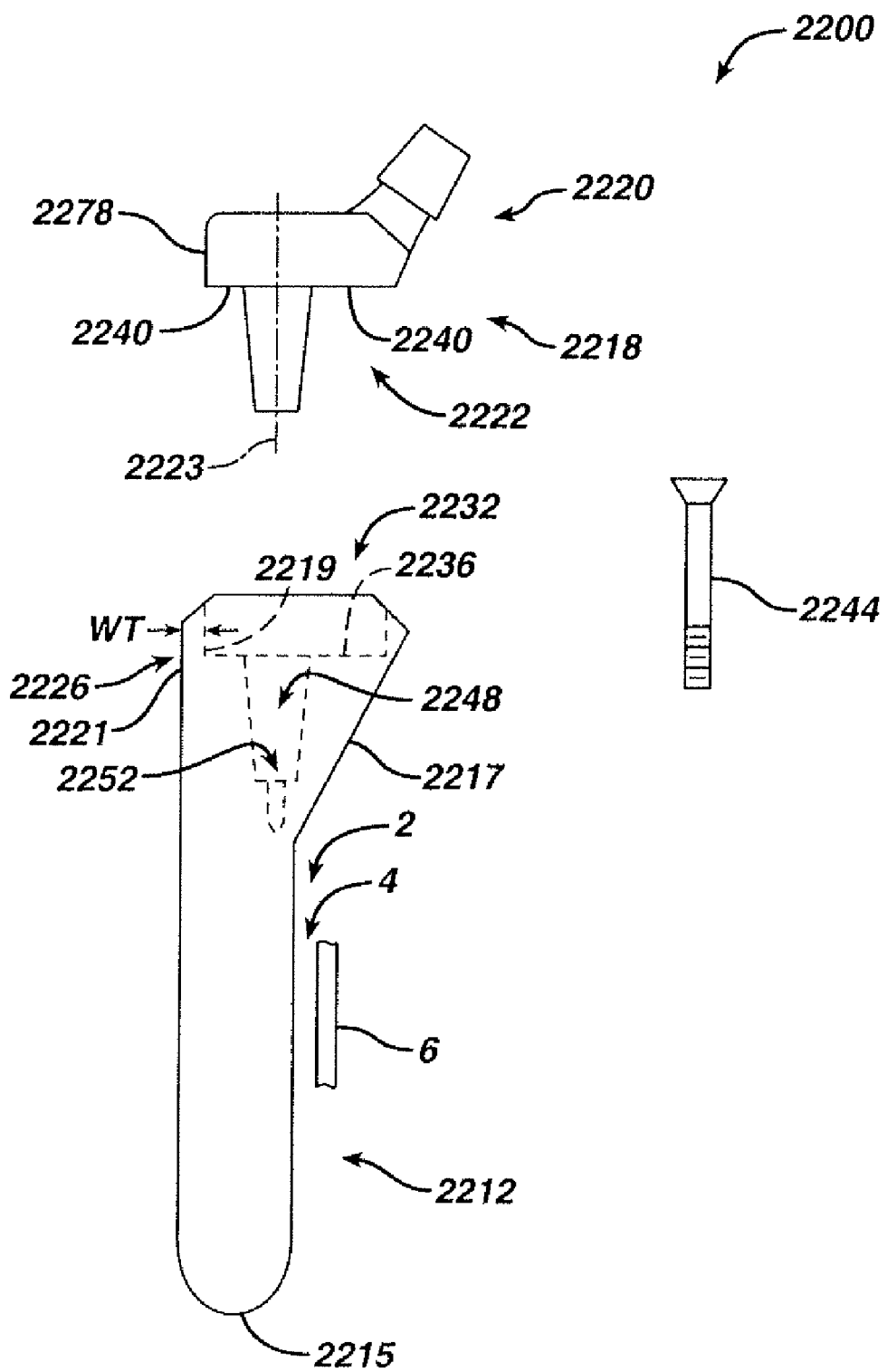
FIG. 27 is a plan view of yet another kit for performing joint arthroplasty including the modular stem of the present invention.

According to the present invention and as shown in FIG. 27, a stem component 2212 for use with a joint component 2218 having a body portion 2220 and a connection portion 2222 in performing joint arthroplasty is provided. The connection portion 2222 of the joint component 2218 has an external periphery 2278. At least a portion of the stem component 2212 may be fitted to cavity 2 in canal 4 of a long bone 6. The stem component 2212 includes a canal portion 2214 having a first end 2215 for insertion into the cavity and an opposed second end 2217.

The stem component 2212 also includes a sleeve portion 2226 extending from the second end 2217 of the canal portion 2214. The sleeve portion 2226 has an internal periphery 2219 that forms an internal cavity 2232. The sleeve portion 2226 has an external periphery 2221. The canal portion 2214 and/or the sleeve portion 2226 may be in removable fixed engagement with the joint component 2218. At least a portion of the external periphery 2221 of the sleeve portion 2226 may be fitted to the cavity 2 of the long bone 6. At least a portion of the external periphery 2278 of the connection portion 2222 of the joint component 2218 may be fitted into the internal cavity 2232 of the sleeve portion 2226, so that the external periphery 2278 of the connection portion 2222 of the joint component 2218 is spaced inwardly from the external periphery 2221 of the sleeve portion 2226 of the stem component 2212 when the joint component 2218 is fixedly connected to the stem component 2212 so that the joint component 2218 may be removed from the long bone 6 without disturbing the fixation of the stem component 2212 to the long bone 6.

As shown in FIG. 27, the stem component 2212 may be configured with a portion 2236 of the external periphery 2221 of the stem component 2212 being generally planar. Further a portion 2240 of the external periphery 2278 of the joint component 2218 may as shown be generally planar. The portion 2236 of the external periphery 2221 of the stem component 2212 and the portion 2240 of the external periphery 2278 of the joint component 2218 as shown in FIG. 27 it should be appreciated are adapted for contact with each other.

The stem component 2212 may as shown in FIG. 27 include a feature 2252 for cooperation with a connector 2244 to connect the stem component 2212 to the joint component 2218. As shown in FIG. 27, the feature 2252 may be in the form of a threaded cavity or in the form of a cylindrical cavity which have been formed in the stem component 2212.

Further and as shown in FIG. 27, the stem component 2212 may include a connection feature 2248 for connection with the joint component 2218. The connection feature 2248 may, as shown, be in the form of a cavity 2248 formed in the stem component 2212. Alternatively, the connection feature (not shown) may be in the form of a cavity. The connection feature 2248 may be tapered.

The stem component 2212 may be in the form of a hip stem 2212. Alternatively the stem component 2212 may be in the form of a tibial implant or a shoulder stem FIGS. 17 and 18 respectively. It should be appreciated that the stem component 2212 may be any component for cooperation with a long bone 6.

The sleeve portion 2226 of the stem component 2212 may define a wall thickness WT thereof. The wall thickness WT may, as shown, be generally uniform about the external periphery 2221 of the sleeve portion 2226 in a plane normal to longitudinal axis 2223 of the joint component 2218. The external periphery 2278 of the connection portion 2222 of the joint component 2218 may, as shown, be adapted to closely conform to the sleeve portion 2226 of the stem component 2212.

It should be appreciated that the stem component 2212 may be interchangeably connected to a variety of joint components 2218 with similar or identical connectors, so that the stem component 2212 can receive joint components of varying heights, offsets and degrees of version.

Although the present invention and its advantages have been described in detail, it should be understood that various changes, substitutions, and alterations can be made therein without departing from the spirit and scope of the present invention as defined by the appended claims.

We claim:

1. A kit for use in performing revision surgery on a cavity in a canal of a long bone, the cavity extending from a resected plane of the long bone, said kit comprising:
   a canal component defining an external periphery thereof, at least a portion of said canal component to be fitted to the cavity in the canal of the long bone, said canal component including a canal portion, said canal portion defining a first end thereof for insertion into the cavity and an opposed second end, said canal component further including a sleeve portion extending from the second end of the canal portion, the sleeve portion having an internal periphery thereof defining an internal cavity thereof in which a portion of the internal periphery of the sleeve portion is planar and is arranged approximately perpendicular to the longitudinal axis of the canal component the sleeve portion also defining an external periphery thereof, wherein a portion of the external periphery of said canal component is generally planar;
   a first joint component removably connectable to the canal component, said first joint component having a neck portion and a connection portion, the neck portion extending from the connection portion at an acute angle and the connection portion of said first joint component defining an external periphery thereof, at least a portion of the external periphery of the connection portion of said first joint component being generally rectangular in shape and being sized and shaped to be fitted into the internal cavity of the sleeve portion of said canal component by virtue of a portion of the external periphery of the connection portion being approximately perpendicular to the longitudinal axis of the canal component;
   a second joint component removably connectable to the canal component, said second joint component having a neck portion and a connection portion, the neck portion extending from the connection portion at an acute angle and the connection portion of said second joint component defining an external periphery thereof, at least a portion of the external periphery of the connection portion of said second joint component being generally rectangular in shape and being sized and shaped to be fitted into the internal cavity of the sleeve portion of said canal component by virtue of a portion of the external periphery of the connection portion being approximately perpendicular to the longitudinal axis of the canal component; and
   a connector to connect the connection portion of one of said first joint component or said second joint component to said canal component, wherein the connector is in contact to both the connection portion of one of said first joint component and said second joint component and said canal component;
   wherein the external periphery of the connection portion of said first joint component is spaced inwardly from the external periphery of the sleeve portion of said canal component when said first joint component is fixedly connected to said canal component so that said first joint component may be removed from the long bone and replaced with said second joint component without disturbing the fixation of said canal component to the long bone;
   wherein the internal cavity of the canal component is sized and shaped to receive the connection portion of the first or second components along the longitudinal axis of the canal component;
   wherein the internal cavity only includes one opening and a portion of the opening is coaxial with the longitudinal axis of the canal component.

2. The kit of claim 1, wherein one of said canal component and said first joint component and said second joint component define a resection ring on a surface thereof, the resection ring adapted for alignment with the resected plane.

3. The kit of claim 1, wherein a portion of said canal component is extendable over a portion of at least one of said first joint component or said second joint component.

4. The kit of claim 1, wherein said first joint component and said second joint component has at least one dimension that is different from each other.

5. The kit of claim 1, wherein said connector comprises a screw.

6. The kit of claim 1, wherein said connector comprises a pin.

7. The kit of claim 1:
wherein the connection comprises
one of said canal component and said first joint component comprises a protrusion extending therefrom; and
wherein the other of said canal component and said first joint component defines an aperture for receiving the protrusion.

8. The kit of claim 7, wherein the protrusion is tapered.

9. The kit of claim 1:
further comprising a prosthetic component adapted for implantation to a second bone, said prosthetic component adapted for cooperation with said first joint component; and
wherein at least a portion of the body portion of said first joint component comprises an articulation surface for articulation with said prosthetic component.

10. The kit of claim 1:
further comprising a prosthetic component for fixed implantation to a second bone and for cooperation with said first joint component; and
a bearing component positionable between said first joint component and said prosthetic component, said bearing component adapted for articulation with at least one of said first joint component and said prosthetic component.

11. The kit of claim 1:
wherein said first joint component comprises a hip neck;
wherein said canal component comprises a hip stem;
further comprising a hip head for attachment to said hip stem; and
further comprising an acetabular cup for articulating cooperation with said hip head.

12. The kit of claim 11:
wherein the connector portion of said first joint component includes a tapered protrusion; and
wherein said canal component defines a cavity for receiving the protrusion.

13. The kit of claim 1:
wherein said canal component defines a longitudinal axis thereof; and
wherein the internal periphery and the external periphery of the sleeve portion of said canal component defines a wall thickness therebetween, the wall thickness being generally uniform in a plane normal to the longitudinal axis of said canal component, the external periphery of said connection portion of said first joint component adapted to closely conform to the internal periphery of the sleeve portion of said canal component.

14. The orthopaedic implant of claim 1:
wherein said canal component comprises a humeral stem;
wherein said first joint component comprises a humeral neck; and
further comprising a humeral head for connection with said humeral neck.

15. A kit for use in performing joint arthroplasty, said kit comprising:
a canal component implant defining an external periphery thereof, at least a portion of said canal component implant to be fitted to a cavity in a canal of a long bone, said canal component implant including a canal portion, the canal portion defining a first end thereof for insertion into the cavity and an opposed second end, said canal component implant further including a sleeve portion extending from the second end of the canal portion, the sleeve portion having an internal periphery thereof defining an internal cavity thereof in which the a portion of the internal periphery of the sleeve portion is planar and is arranged approximately perpendicular to the longitudinal axis of the canal component, the sleeve portion also having an external periphery thereof, wherein a portion of the external periphery of said canal component implant is generally planar;
a first joint component implant removeably connectable to said canal component implant, said first joint component implant having a neck portion and a connection portion, the neck portion extending from the connection portion at an acute angle and the connection portion of said first joint component implant defining an external periphery thereof, at least a portion of the external periphery of the connection portion of said first joint component implant being generally rectangular in shape and being sized and shaped to be fitted into the internal cavity of the sleeve portion of said canal component implant, so that the external periphery of the connection portion of said first joint component implant is spaced inwardly from the external periphery of the sleeve portion of said canal component implant when said first joint component implant is fixedly connected to said canal component implant so that said first joint component implant may be removed from the long bone without disturbing the fixation of said canal component implant to the long bone by virtue of a portion of the external periphery of the connection portion being approximately perpendicular to the longitudinal axis of the canal component;
a first joint component trial generally corresponding in size and shape with said first joint component implant, said first joint component trial being removeably connectable to said canal component implant, said first joint component trial having a body portion and a connection portion, the connection portion of said first joint component trial defining an external periphery thereof, at least a portion of the external periphery of the connection portion of said first joint component trial being generally rectangular in shape and being sized and shaped to be fitted into the internal cavity of the sleeve portion of said canal component implant, so that the external periphery of the connection portion of said first joint component trial is spaced inwardly from the external periphery of the sleeve portion of said canal component implant when said first joint component trial is fixedly connected to said canal component implant so that said first joint component trial may be removed from the long bone without disturbing the fixation of said canal component implant to the long bone;
a second joint component implant removeably connectable to said canal component implant, said second joint component implant having a neck portion and a connection portion, the neck portion extending from the connection portion at an acute angle and the connection portion of said second joint component implant defining an external periphery thereof, at least a portion of the external periphery of the connection portion of said second joint component implant being generally rectangular in shape and being sized and shaped to be fitted into the internal cavity of the sleeve portion of said canal component implant, so that the external periphery of the connection portion of said second joint component implant is spaced inwardly from the external periphery of the sleeve portion of said canal component implant when said second joint component implant is fixedly connected to said canal component implant so that said second joint component implant may be removed from the long bone without disturbing the fixation of said canal component implant to the long bone by virtue of a portion of the external periphery of the connection portion being approximately perpendicular to the longitudinal axis of the canal component;

a second joint component trial generally corresponding in size and shape with said second joint component implant, said second joint component trial being removeably connectable to said canal component implant, said second joint component trial having a body portion and a connection portion, the connection portion of said second joint component trial defining an external periphery thereof, at least a portion of the external periphery of the connection portion of said second joint component trial being generally rectangular in shape and being sized and shaped to be fitted into the internal cavity of the sleeve portion of said canal component implant, so that the external periphery of the connection portion of said second joint component trial is spaced inwardly from the external periphery of said sleeve portion of said canal component implant when said second joint component trial is fixedly connected to said canal component implant so that said second joint component trial may be removed from the long bone without disturbing the fixation of said canal component implant to the long bone, said kit permitting said canal component implant to be permanently implanted and said first joint component trial to be assembled to said canal component implant and used to perform a trial reduction and replaced with said second joint component trial if the trial reduction has unsatisfactory results; and a connector to connect the connection portion of one of said first joint component, said first joint component trial, said second joint component, or said second joint component trial to said canal component, wherein the connector is in contact to both the connection portion of one of said first joint component or said second joint component and said canal component;

wherein the internal cavity of the canal component is sized and shaped to receive the connection portion of the first joint component, first joint component trial, second joint component or second joint component trial along the longitudinal axis of the canal component;

wherein the internal cavity only includes one opening and a portion of the opening is coaxial with the longitudinal axis of the canal component.

* * * * *